US012665807B1

(12) United States Patent　　　(10) Patent No.:　US 12,665,807 B1

Jukic et al.　　　(45) Date of Patent:　Jun. 23, 2026

(54) SYSTEM AND METHOD FOR RETROFIT DEPLOYMENT OF A VENDOR-AGNOSTIC MEDICAL DEVICE INTEGRATION INFRASTRUCTURE

(71) Applicant: OneSource Solutions International, Inc., Sudbury, MA (US)

(72) Inventors: Vedran Jukic, Trieste (IT); Harold Arkoff, Sudbury, MA (US)

(73) Assignee: OneSource Solutions International Inc., Sudbury, MA (US)

( * ) Notice: Subject to any disclaimer, the term of this patent is extended or adjusted under 35 U.S.C. 154(b) by 0 days.

(21) Appl. No.: 19/452,563

(22) Filed: Jan. 19, 2026

Related U.S. Application Data

(60) Provisional application No. 63/786,132, filed on Apr. 9, 2025, provisional application No. 63/748,623, filed on Jan. 23, 2025.

(51) Int. Cl.
| | |
|---|---|
| *G06F 15/177* | (2006.01) |
| *A61B 90/00* | (2016.01) |
| *A61B 90/90* | (2016.01) |
| *G16H 40/67* | (2018.01) |
| *H04L 9/40* | (2022.01) |
| *H04L 41/0803* | (2022.01) |
| *H04L 67/12* | (2022.01) |

(52) U.S. Cl.
CPC .......... *H04L 41/0803* (2013.01); *A61B 90/08* (2016.02); *A61B 90/90* (2016.02); *G16H 40/67* (2018.01); *H04L 63/08* (2013.01); *H04L 67/12* (2013.01)

(58) Field of Classification Search
None
See application file for complete search history.

(56) References Cited

U.S. PATENT DOCUMENTS

| | | | | |
|---|---|---|---|---|
| 7,013,365 | B2 * | 3/2006 | Arnouse | .............. G06Q 20/341 711/115 |
| 11,850,439 | B2 * | 12/2023 | Freeman | .............. A61N 1/0476 |
| 2007/0255348 | A1 * | 11/2007 | Holtzclaw | .............. G16H 40/67 607/60 |
| 2011/0307274 | A1 * | 12/2011 | Thompson | .............. G16H 10/60 717/173 |

(Continued)

*Primary Examiner* — Phuoc H Nguyen
(74) *Attorney, Agent, or Firm* — IP Consulting Group; Michael Razavi; Alfred F. Hoyte, Jr.

(57) ABSTRACT

A retrofit medical device integration infrastructure is disclosed for deployment in already-built healthcare facilities without structural renovation. Modules install at or near existing bedside wall locations, including outlet positions and wall plates, using existing wall boxes or surface enclosures and building services. Device-interface modules couple to heterogeneous medical devices to acquire outputs at the point of care. Wall-mounted distribution components and edge processing units establish a hospital-owned clinical integration plane isolated from a general facility IT network. Outputs are normalized into standardized data objects including device identity, location association, and time information, and routed through authorized communication paths to downstream systems. Coexistence with incumbent vendor monitoring is supported by acquiring parallel copies without disrupting primary workflows. Optional buffering and alternate uplinks provide resilience during connectivity disruption.

14 Claims, 7 Drawing Sheets

(56)        References Cited

U.S. PATENT DOCUMENTS

2016/0135706 A1*   5/2016   Sullivan ............... A61B 5/7267
                                                              600/509
2016/0156599 A1*   6/2016   Son .................... H04L 63/0464
                                                              713/168
2018/0317826 A1*   11/2018  Muhsin ............. A61B 5/14552
2020/0402651 A1*   12/2020  Nesterenko ........... G16H 40/20
2022/0096825 A1*   3/2022   McDonald ............... A61N 1/08

* cited by examiner

SYSTEM AND METHOD FOR RETROFIT DEPLOYMENT OF A VENDOR-AGNOSTIC MEDICAL DEVICE INTEGRATION INFRASTRUCTURE

CROSS-REFERENCE TO RELATED APPLICATIONS

This application claims the benefit of priority under 35 U.S.C. § 119(e) to: (i) U.S. Provisional Patent Application No. 63/748,623, filed Jan. 23, 2025, titled "System and Methods for Medical Device Integration and Scalable Deployment"; and (ii) U.S. Provisional Patent Application No. 63/786,132, filed Apr. 9, 2025, titled "Infrastructure-Embedded Vendor-Agnostic Medical Device Integration System for Hospital-Owned AI Ready Data Governance," the entire contents of each of which are incorporated herein by reference.

This application is related to other U.S. patents and applications owned by the Applicant that describe components and embodiments usable with the disclosed retrofit device-integration architecture, including, by way of example: U.S. Provisional Application No. 62/804,838 (filed Feb. 13, 2019); U.S. Pat. No. 11,309,665 B1 (issued Apr. 19, 2022) titled "Active Cable Arrangement for Connecting Medical Devices to a Display"; U.S. Pat. No. 11,693,990 B1 (issued Jul. 4, 2023) titled "Medical Data Governance"; and U.S. Pat. No. 12,001,464 B1 (issued Jun. 4, 2024) titled "System and Method for Medical Data Governance Using Large Language Models," the entire disclosures of which are incorporated herein by reference.

FIELD OF THE INVENTION

The present invention relates to the field of medical device integration infrastructure within healthcare facilities. More particularly, the invention relates to physical and logical integration architectures that enable medical devices to be connected, managed, and governed within existing healthcare environments through retrofit deployment. The invention is directed to vendor-agnostic integration systems that can be installed in already-built rooms, wards, and care areas using attach-on components and existing building services, including existing electrical outlets and existing wired network connections, without requiring structural renovation or replacement of incumbent medical devices.

The invention further relates to infrastructure-level mechanisms for acquiring medical device outputs at or near the point of care, normalizing heterogeneous device data, and producing standardized, governance-ready data objects suitable for secure transport to downstream monitoring, documentation, analytics, and artificial intelligence systems. The disclosed architectures are applicable to fixed inpatient rooms as well as mobile, temporary, and surge care environments, and are designed to preserve coexistence with existing vendor monitoring pathways while enabling hospital-owned, scalable deployment of governed medical device integration capabilities.

BACKGROUND OF THE INVENTION

Healthcare facilities increasingly operate under conditions that require rapid expansion, reconfiguration, or redistribution of monitored care capacity. Such conditions arise during patient surges, disasters, public health emergencies, or routine operational constraints that require conversion of non-critical-care spaces into monitored environments. In these scenarios, medical devices must be deployed quickly and reliably at the point of care, often in locations not originally designed to support advanced monitoring or data integration. Existing rooms, overflow wards, temporary structures, and repurposed spaces may lack the cabling, network infrastructure, or embedded systems typically associated with modern intensive care units, yet still require equivalent levels of device connectivity, monitoring continuity, and data availability.

Conventional approaches to medical device integration have been developed primarily for static, vendor-controlled environments and typically rely on specialized vendor-specific intermediary devices, proprietary protocols, dedicated cabling, and per-room engineering. Such approaches are poorly suited to rapid or incremental deployment, particularly in already-built facilities where structural renovation, installation of new conduit, or extended downtime is impractical or prohibited. Moreover, these approaches often assume exclusive control over device connectivity, making it difficult to preserve incumbent monitoring pathways while simultaneously introducing additional data feeds for documentation, analytics, or emerging computational systems.

Hospitals have historically treated critical clinical utilities—such as electrical power and medical gases—as standardized, room-agnostic services that can be brought reliably to the bedside regardless of device manufacturer or clinical workflow. In contrast, medical device data connectivity has evolved in a fragmented and vendor-specific manner, resulting in bespoke integration architectures that vary from room to room and from vendor to vendor. As a consequence, there has been no widely deployable equivalent of a standardized clinical "data utility" that can be retrofitted into existing environments with the same predictability, reliability, and neutrality as other bedside utilities.

Traditional medical device integration solutions have also been shaped by regulatory and operational incentives that prioritize low-frequency data capture for electronic medical record population rather than continuous, high-fidelity data availability. Many such systems were designed to meet minimum documentation requirements, often capturing data at coarse time intervals, and do not support the timing precision, buffering, or contextual attribution required for real-time monitoring, advanced analytics, or high-frequency event detection. As a result, these solutions are ill-suited to emerging clinical workflows that depend on continuous telemetry, precise temporal alignment, and reliable attribution of data to devices, locations, and patients.

Vendor-controlled intermediary devices and proprietary middleware further constrain interoperability by anchoring integration to single-vendor ecosystems. Hospitals are frequently required to deploy multiple parallel integration systems to accommodate devices from different manufacturers, increasing complexity, cost, and maintenance burden. These systems often require ongoing configuration, specialized expertise, and third-party support, and may lack consistent cybersecurity controls or network-level enforcement of regulatory requirements. In addition, vendor-centric architectures create incentives to replace intermediary devices rather than to integrate heterogeneous equipment under a neutral, hospital-owned framework.

Implementing a neutral integration layer across heterogeneous medical devices presents additional technical challenges in safety-critical environments. These challenges include accommodating diverse physical interfaces and communication protocols, preserving coexistence with incumbent vendor central stations, maintaining continuity during network disruptions, enforcing cybersecurity and access controls at the point of acquisition, and ensuring accurate association between device outputs, physical location, and patient identity as equipment is moved or shared. Conventional solutions often rely on manual processes for patient and device association, increasing the risk of misattribution, delayed interventions, and compromised patient safety.

The limitations of legacy integration architectures have become increasingly apparent with the emergence of artificial intelligence and advanced computational systems in healthcare. These systems require continuous, high-resolution, context-aligned data streams that exceed the capabilities of traditional integration methods. At the same time, healthcare environments are incorporating a growing diversity of data sources, including patient-worn devices, auxiliary sensors, infusion systems, and wireless measurement technologies. Existing integration approaches lack a unified framework for validating, governing, and securely transporting such data without imposing vendor lock-in or requiring invasive infrastructure changes.

Many hospitals and clinics were constructed long before the availability of modern, AI-ready medical device integration architectures. Retrofitting these facilities with infrastructure-embedded solutions—such as fixed wall panels, built-in ports, or integrated device mounts—often requires invasive construction, regulatory approvals, extended downtime, and substantial capital expenditure. As a result, healthcare providers remain dependent on legacy vendor-specific intermediary devices and cabling layouts that are difficult to modernize and that do not provide standardized, governed data outputs suitable for contemporary clinical and computational workflows.

Accordingly, there exists a need for a medical device integration infrastructure that can be deployed as a retrofit into existing healthcare environments using attach-on components and existing building services, without structural renovation and without disruption of incumbent clinical workflows. Such an infrastructure should support vendor-agnostic device connectivity, preserve coexistence with existing monitoring systems, maintain accurate device-location-patient association, and provide standardized, governance-ready data streams capable of supporting modern monitoring, documentation, analytics, and artificial intelligence systems. The present invention is directed to addressing these needs by establishing a retrofit-deployable, hospital-owned integration infrastructure that functions as a durable clinical utility rather than as a vendor-specific integration product.

SUMMARY OF THE INVENTION

The invention is directed primarily to retrofit deployment of a medical device integration infrastructure in existing healthcare facilities without structural renovation. In disclosed embodiments, the infrastructure is installed at or proximate to existing bedside wall locations—such as electrical outlet positions, switch plates, or low-voltage terminations—using standard wall boxes, surface-mounted enclosures, or equivalent mounting structures already present in the facility. Installation does not require wall demolition, new conduit installation, ceiling modification, or per-room network engineering, and may be performed by facilities personnel or other non-specialist installers with minimal disruption to ongoing clinical operations.

In this disclosure, retrofit deployment without structural renovation is treated as a primary embodiment. Wall-embedded, behind-wall, and other concealed installations are described as optional packaging or installation variants, and do not limit the scope of the invention.

The invention addresses a technical and operational problem inherent in legacy healthcare environments, in which hospitals contain large inventories of heterogeneous medical devices acquired over extended periods from multiple manufacturers. These devices are frequently coupled to proprietary vendor-specific intermediary devices, vendor-specific central stations, and tightly integrated workflows that cannot be removed, replaced, or reconfigured without disrupting patient care. Existing facilities further impose constraints distinct from new construction, including limited ability to modify walls or cabling infrastructure, requirements to preserve incumbent monitoring pathways, and the need to avoid downtime during deployment.

To address these constraints, the disclosed invention provides a hospital-owned, vendor-agnostic integration infrastructure that can be deployed using existing building services and attach-on components, without requiring replacement or modification of existing medical devices. Unlike conventional vendor-specific intermediary devices, middleware software platforms, or infrastructure embedded during new construction, the invention is specifically designed for retrofit deployment in already-built rooms, wards, and mobile clinical environments using existing electrical outlets, existing network drops, and standardized cabling practices.

In disclosed embodiments, the infrastructure establishes a controlled clinical integration plane formed by cooperating physical components. Individual medical devices are coupled to corresponding device-interface modules that acquire device output data using device-specific physical interfaces and protocol handling, without altering device operation. The device-interface modules normalize heterogeneous device outputs into standardized internal representations suitable for governed downstream use. Power and data connectivity for the device-interface modules is provided by wall-mounted or wall-adjacent distribution components installed at or near existing electrical outlet locations. An edge processing component operates as the network authority for the clinical integration plane, enforcing authentication, authorization, isolation from the general hospital information technology network, time alignment, buffering, logging, and secure routing of standardized data objects to downstream destinations.

A defining characteristic of the invention is its explicit support for coexistence with incumbent vendor monitoring systems. In retrofit deployments, medical devices may continue to communicate with existing vendor-specific intermediary devices or central stations over their primary communication pathways, while the disclosed device-interface modules obtain a parallel copy of device outputs using non-intrusive capture mechanisms. Primary clinical workflows remain unchanged, and the disclosed infrastructure operates independently to produce standardized, governance-ready data objects under hospital control. This coexistence capability enables incremental deployment without disrupting patient care and avoids forcing hospitals into single-vendor ecosystems.

The standardized outputs produced by the infrastructure include device identity information, physical location context derived from controlled connection points or predefined templates, time information used to preserve ordering and support buffering and replay, and provenance fields supporting auditability and policy enforcement. By emitting governed, context-aligned data objects rather than raw vendor-specific signals, the infrastructure decouples bedside device heterogeneity from downstream monitoring, documentation, analytics, and artificial intelligence systems. Downstream systems therefore operate on trusted, standardized inputs without requiring direct coupling to device-specific protocols or vendor-specific intermediary devices.

The infrastructure is designed to function as a retrofit-deployable hospital utility, analogous in operational necessity to power, medical gases, and network access. Configuration may be derived automatically from predefined templates or centralized configuration services, allowing large numbers of legacy rooms to be upgraded without bespoke per-room engineering. Devices may be added, replaced, moved, or swapped during routine clinical operations, with the infrastructure automatically maintaining correct device-location association and auditability.

In some embodiments, the infrastructure provides resilient transport mechanisms to maintain continuity of governed data capture when conventional networking is unavailable or degraded. Such mechanisms may include local buffering and store-and-forward operation, wired and wireless failover, secure self-configuring mesh networking, and controlled use of existing facility electrical wiring as a backhaul path. These embodiments enable deployment in temporary, mobile, or surge environments, including transport settings, pop-up wards, and repurposed clinical spaces, while preserving a consistent data model and governance framework.

The invention is not limited to any specific downstream application, analytics engine, or artificial intelligence system. Its technical contribution lies in the creation of a concrete, physical integration infrastructure that acquires medical device outputs at the point of care, normalizes and attributes those outputs under hospital-defined governance, and delivers standardized data objects through secure, controlled transport paths. By converting legacy clinical environments into governed, AI-ready data sources without structural renovation or device replacement, the invention provides a scalable foundation for modern monitoring, documentation, analytics, and artificial intelligence workflows while preserving incumbent vendor operation and clinical safety.

BRIEF DESCRIPTION OF THE DRAWINGS

The accompanying drawings, which are incorporated herein and form a part of this specification, illustrate embodiments of the disclosed subject matter and, together with the description, serve to explain the principles of the invention.

DETAILED DESCRIPTION OF THE INVENTION

Figure 1:
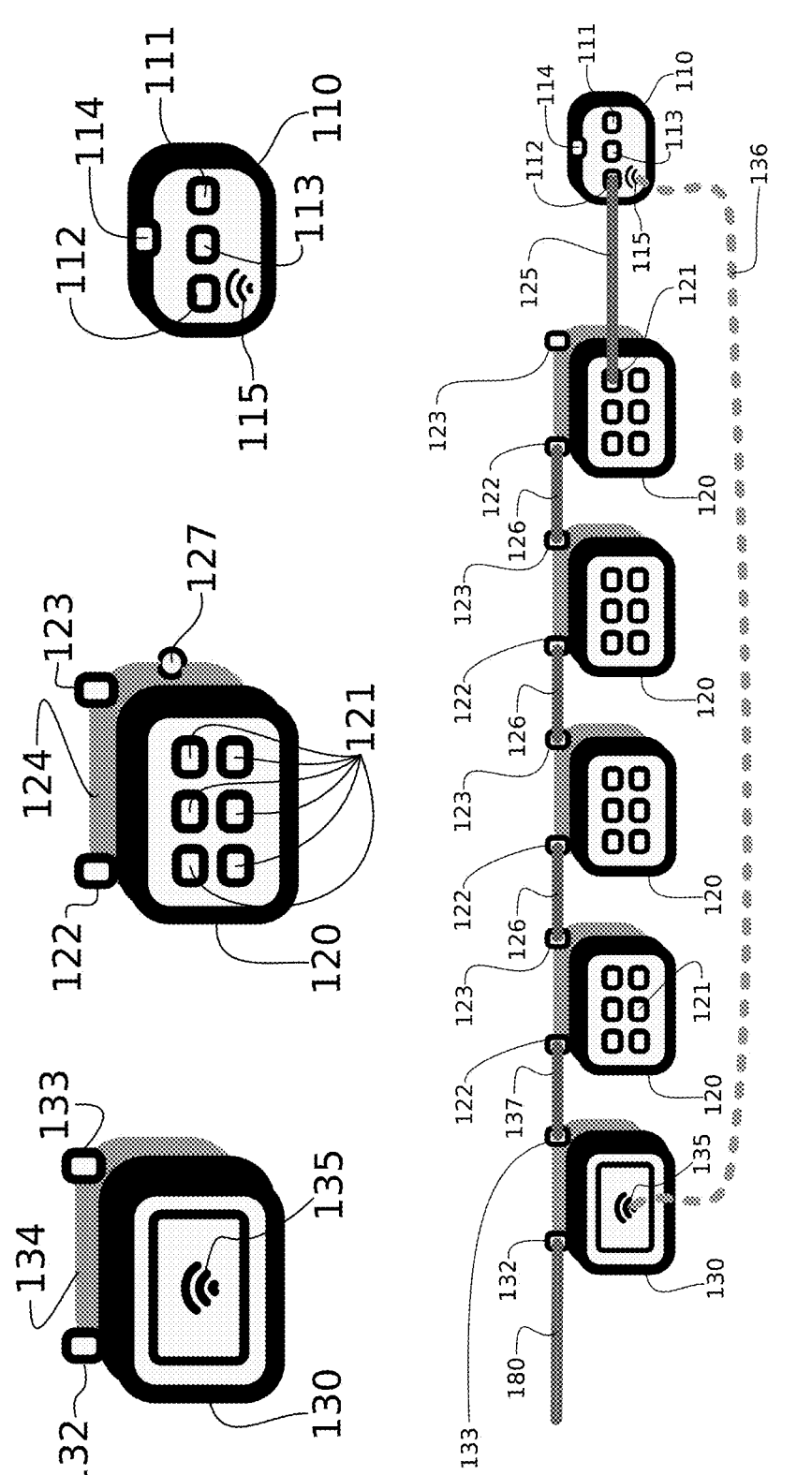
FIG. 1 is a schematic diagram illustrating an example medical device integration system comprising a device-interface module coupled to a medical device, a wall-mounted, wall-adjacent, or wall-associated power-and-data distribution component, an edge processing unit, and a remote management system.

The invention disclosed herein relates to a physical and logical medical device integration infrastructure designed first and foremost for retrofit deployment in already-built healthcare facilities without structural renovation. In the disclosed embodiments, integration components are installed at existing bedside locations, including electrical outlet positions, switch plates, and low-voltage wall plate locations, using standard wall boxes, surface-mounted enclosures, or equivalent mounting structures already present in the facility. No wall demolition, ceiling modification, new conduit installation, or structural alteration is required to practice the invention.

Installation may be performed by facilities personnel or other non-specialist installers using conventional electrical and low-voltage mounting practices, without per-room software engineering or bespoke network configuration. The infrastructure is therefore suitable for rapid deployment, incremental rollout, and minimal downtime in active clinical environments, including legacy patient rooms, wards, and temporary or surge care areas.

Although some embodiments may package components partially or fully within an existing wall cavity, such in-wall packaging represents an optional physical form factor and is not required to practice the invention. Surface-mounted, wall-adjacent, behind-wall, cart-mounted, rail-mounted, or pole-mounted deployments provide equivalent functional behavior and are expressly within the scope of the disclosure.

Existing healthcare facilities typically include heterogeneous bedside equipment acquired over extended periods from multiple manufacturers and accompanied by vendor-specific intermediary devices, proprietary central stations, and tightly coupled workflows that cannot be removed or reconfigured without disrupting patient care. Such environments impose constraints fundamentally different from new construction, including limited ability to open walls, limited availability of new network cabling, restrictions on downtime, and requirements to preserve incumbent monitoring and documentation pathways. The disclosed invention addresses these constraints by providing a hospital-owned integration infrastructure that uses existing building services and attach-on components to unify device outputs into a consistent, governed data fabric without redesigning rooms, replacing devices, or performing per-room network engineering.

In the disclosed embodiments, the infrastructure establishes a controlled clinical integration plane formed by cooperating physical components. A device-interface module is coupled to a medical device and acquires device output data using device-specific physical interfaces and protocol handling, without altering device operation. A wall-mounted or wall-adjacent power-and-data distribution component provides power delivery and data transport to one or more device-interface modules using standardized cabling while maintaining a defined isolation boundary for clinical device traffic. A wall-mounted or wall-adjacent edge processing component acts as the local network authority for the clinical integration plane, enforcing authentication, authorization, time alignment, buffering, logging, and secure routing of standardized data objects to downstream destinations under hospital control.

A defining characteristic of the invention is its explicit support for coexistence with incumbent vendor monitoring pathways that remain necessary for patient care. In retrofit deployments, medical devices may continue to communicate with existing vendor-specific intermediary devices or central stations over their primary communication paths, while the disclosed device-interface modules obtain a parallel copy of device outputs using pass-through connectors, mirrored ports, inline adapters, or other non-intrusive capture mechanisms selected to avoid interference with the primary pathway. In such embodiments, the incumbent workflows remain unchanged, while the disclosed infrastructure independently produces standardized, governance-ready data objects.

The standardized outputs produced by the infrastructure are structured to support integrity, attribution, and downstream governance. In some embodiments, standardized data objects include device identity information, physical location context derived from installation points or assigned room templates, time information used to preserve ordering and support buffering and replay, and provenance fields supporting auditability and policy enforcement. By emitting governed, context-aligned data objects rather than raw vendor signals, the infrastructure decouples bedside device heterogeneity from downstream monitoring, documentation, analytics, and artificial intelligence systems.

The disclosed infrastructure is intended to function as a deployable hospital utility, analogous in operational role to power, medical gases, or network access. Installation may be performed using existing electrical and network services, and configuration may be derived from predefined room templates or centralized configuration services, allowing large numbers of legacy rooms to be rendered AI-ready without bespoke per-room engineering. Devices may be added, replaced, moved, or swapped during routine clinical operations, with the infrastructure automatically maintaining correct device-location association and auditability.

In addition to routine inpatient rooms, the infrastructure may be deployed in mobile and temporary clinical environments, including transport settings, surge units, and pop-up care areas. In such deployments, the same core components may be mounted on carts, rails, poles, or temporary structures and coupled to available power and backhaul resources. Where conventional facility networking is unavailable or degraded, certain embodiments provide optional resilient transport mechanisms, including buffering and store-and-forward behavior, wireless fallback, secure mesh routing, and controlled use of communication over existing electrical wiring.

The embodiments described herein are directed primarily to the infrastructure for device data acquisition, normalization, attribution, secure transport, and governance in retrofit environments. Downstream functions such as visualization, analytics, artificial intelligence, alerting, or control may be supported using the standardized outputs produced by the infrastructure, but such downstream functions are not required to practice the invention. The practical effect of the disclosed architecture is to convert legacy, heterogeneous clinical environments into governed, standardized data sources suitable for modern clinical and computational workflows while preserving incumbent device operation and avoiding structural renovation.

DEFINITIONS AND TERMINOLOGY

As used herein, the term "AI-ready" refers to a property of data outputs produced by the infrastructure, in which medical device data is captured, time-aligned, location-bound, and delivered in a standardized, machine-consumable form with sufficient provenance fields, including at least device identity, physical location, and time information. The term "AI-ready" does not imply that the infrastructure performs artificial intelligence, clinical inference, diagnosis, or treatment selection, but rather that the standardized outputs are suitable for consumption by downstream computational systems, including analytics or artificial intelligence systems, operating outside the infrastructure.

As used herein, the term "governance-ready" refers to standardized data objects that include fields enabling downstream policy enforcement, auditability, and access control, such as identifiers, timestamps, and contextual tags, without requiring modification of underlying legacy devices.

In some embodiments, a "governance-ready data object" comprises, by way of example, a structured record including a device identifier, a location identifier, time information such as a timestamp and/or time source, one or more measurement values and associated units, and provenance fields indicating an acquisition interface or protocol, optional quality flags, and/or contextual tags. In some embodiments, the object further includes an optional integrity field such as a hash or signature over at least a portion of the object.

As used herein, the term "existing network drop" refers to a pre-existing network access point of a facility, such as a wired Ethernet port, bedside network connection, or facility-provided wireless access, available without structural renovation or new conduit installation.

As used herein, the term "configuration service" refers to one or more software components, which may be executed on an edge processing unit, a local server, or a cloud service, configured to enroll modules, apply templates, assign location identifiers and device roles, and manage routing rules for standardized data objects.

As used herein, the term "coexistence mode" refers to an operating mode in which a legacy medical device continues to communicate with a vendor-specific intermediary devices over an existing primary communication path while an integration module obtains a copy of corresponding device outputs via a secondary interface, duplicated output, non-intrusive tap, or parallel data connection, such that vendor workflows remain unchanged.

As used herein, the term "zero-configuration deployment" refers to installation and activation of retrofit components without requiring a skilled integrator to manually configure device drivers, network routes, or room-specific settings, wherein device enrollment, room assignment, and data routing are performed automatically based on templates, discovery events, and governance policies.

As used herein, the term "device-patient association" refers to a governed mapping that links a specific medical device or sensor stream to a patient identifier and a physical location or care area, including temporal validity, such that downstream systems can attribute telemetry correctly even when equipment is moved or swapped.

As used herein, the term "non-display interface" refers to an interaction modality that does not require a dedicated screen at the point of care, including voice-based interaction via microphone and/or speaker arrays, gesture or presence detection, and other ambient interfaces coupled to the retrofit infrastructure.

As used herein, the term "augmented clinical reality" refers to a fused, governed representation of patient state and clinical context derived from multiple sensing sources, including bedside devices, environmental sensors, and wearables, and made available to clinical workflow systems and AI services for context-aware monitoring, guidance, and/or control actions.

As used herein, the term "secure mesh network" refers to a self-configuring network formed between multiple retrofit modules that provides encrypted communication paths independent of, or redundant to, facility IT networks. In some embodiments, the mesh includes powerline communication over existing electrical wiring and/or wireless links for failover connectivity.

As used herein, the term "closed-loop control" refers to a workflow in which sensed physiologic or contextual measurements are used to trigger governed actions including alarms, notifications, workflow tasks, and/or device control commands and wherein the actions are validated against safety and policy constraints prior to execution.

As used herein, the term "template" refers to a stored configuration profile for a legacy room type that specifies expected device roles, location identifiers, security and network policies, and associated routing rules for standardized data objects, such that deployment can be performed without per-room engineering.

As used herein, the term "routing rule" refers to a machine-executable policy or mapping that directs standardized data objects to one or more destinations based on device role, patient context, location, data type, time, priority, and/or compliance constraints.

As used herein, the term "clinical integration plane" refers to a controlled physical and logical network environment that exists between medical devices at the point of care and downstream systems, and that is distinct from a general hospital information technology network. The clinical integration plane includes device-interface modules, controlled power-and-data distribution components, and one or more edge processing units that collectively enforce authorization, isolation, and governance at the point of data acquisition. Medical devices and device-interface modules within the clinical integration plane are prevented from obtaining direct connectivity to the general hospital information technology network, and all ingress and egress of device data is mediated by an edge processing unit that enforces authentication, authorization, and routing policies. In some embodiments, enforcement of the clinical integration plane includes one or more of network segmentation, port-level control, authenticated enrollment, device whitelisting, and controlled uplink routing, such that systems and networks outside the clinical integration plane do not obtain direct access to devices within the plane.

As used herein, the term "non-interference" refers to a technical condition in which acquisition of a parallel copy of medical device output data does not interrupt, delay, modify, inject, or otherwise affect a primary communication pathway between the medical device and an incumbent vendor monitoring system. In non-interfering configurations, failure or unavailability of the parallel acquisition path does not impair operation of the primary vendor pathway, which continues uninterrupted.

As used herein, the term "standardized data object" refers to a structured, machine-consumable data record generated within the clinical integration plane from normalized device output data. In some embodiments, a standardized data object includes, at minimum, device identity information identifying the originating medical device or device-interface module, a location identifier derived from physical installation context, time information including a timestamp and/or ordering information sufficient to preserve sequence and time integrity, one or more measurement values with associated units, and provenance or quality fields indicating acquisition source, interface type, or validation status. In some embodiments, standardized data objects may be encoded using structured representations such as JSON, CBOR, or Protocol Buffers, although no specific encoding format is required.

As used herein, the term "existing bedside outlet location" refers to a physical location within a patient care area that includes an existing electrical outlet, switch plate, or low-voltage wall plate installed as part of a facility's original or prior construction. Such a location includes the associated wall box, enclosure, or conduit zone serving the outlet or plate. Installation "at or proximate to" an existing bedside outlet location refers to installation within the same patient bay or care area and functionally associated with the same wall location, without requiring new conduit, structural modification, or relocation of existing building services.

As used herein, the term "standard wall box" refers to a conventional electrical or low-voltage enclosure used for outlets, switches, or terminations, and the term "surface-mounted enclosure" refers to an enclosure mounted on a wall surface without opening or modifying the wall structure. Use of a wall cavity is optional and not required to practice the invention.

As used herein, the term "port identity" refers to a persistent identifier associated with a physical powered connection port of a power-and-data distribution component. In some embodiments, the port identity includes one or more of a physical port number, a network interface identifier, and a unique identifier of the hosting distribution component.

The port identity persists across power cycles and is used by an edge processing unit to associate a physical connection event with a corresponding location identifier. Movement of a device-interface module between ports results in reassignment of the location identifier based on the port identity.

As used herein, the term "configuration drift" refers to a deviation between an actual deployment state of devices, ports, or associations and an expected state defined by a template. In some embodiments, validation rules defined by the template are applied to detect missing, duplicated, misassigned, or unauthorized device roles, port associations, or routing behaviors.

As used herein, the term "Structural renovation" refers to physical modification of a building's fixed infrastructure that alters or penetrates permanent structural or utility elements, including but not limited to cutting or opening walls, ceilings, or floors; installing or rerouting in-wall or in-ceiling electrical wiring, conduits, plumbing, or network cabling; modifying load-bearing components; or performing construction activities requiring building permits or room decommissioning. Structural renovation does not include surface-mounted installation, attachment, or replacement of devices using existing outlets, ports, mounting points, wall plates, raceways, or externally accessible interfaces, nor does it include plug-and-play deployment, bedside attachment, pole-mounted attachment, or other retrofit installation techniques that preserve existing room infrastructure.

As used herein, the term "secured communication path" refers to a communication channel configured to protect data against unauthorized access, interception, or tampering through one or more security mechanisms.

Automatic Operations Upon Installation and Enrollment

In some embodiments, upon installation and enrollment of retrofit components, the system automatically discovers a management endpoint and establishes a secure session, identifies an attached device type and selects a corresponding protocol driver, assigns or validates a location identifier based on a room template, labeled network drop, or enrollment scan, and generates standardized data objects that include at least a device identifier, a location identifier, and time information. In some embodiments, the system time-synchronizes standardized data objects across multiple modules, buffers standardized data objects locally during network disruption and replays buffered data when connectivity resumes, dynamically routes standardized data objects over wired and/or wireless backhaul links based on link health, and applies policy tags or routing rules to direct standardized data objects to monitoring, documentation, governance, and AI services.

Avoidance of Abstract Clinical Determinations

The embodiments described herein are directed to a physical and logical retrofit infrastructure for acquiring medical device outputs at the point of care, normalizing heterogeneous device data, associating such outputs with device identity, physical location, and time information, and securely routing standardized data objects under hospital-defined governance policies. The disclosed infrastructure does not perform clinical interpretation, diagnosis, treatment selection, or therapeutic decision-making. Its technical contribution resides in controlled physical deployment, authorized data acquisition, normalization, attribution, isolation, and governed transport of device outputs within a clinical integration plane. Any clinical interpretation, alerting, analytics, or artificial intelligence processing based on the standardized data objects is performed, if at all, by downstream systems external to the infrastructure and is not required to practice the invention.

Retrofit Deployment without Structural Renovation

The invention is primarily directed to retrofit deployment in existing healthcare facilities, enabling legacy patient rooms, wards, and mobile clinical environments to be upgraded to a governed, AI-ready state without requiring structural renovation. Retrofit deployment is achieved using attach-on and wall-mounted infrastructure components that leverage existing building services, including electrical power and wired network connections already present at the point of care.

In retrofit embodiments, installation does not require demolition of walls, installation of new conduit, or reconfiguration of existing room layouts. Instead, core infrastructure components are mounted on, within, or adjacent to existing wall locations commonly used for electrical outlets or low-voltage network terminations. By anchoring deployment to these ubiquitous bedside locations, the system enables consistent placement across heterogeneous rooms while preserving existing clinical workflows and room construction.

Installation of the wall-mounted or in-wall infrastructure components may be performed using standard electrical and low-voltage wiring practices applicable to healthcare facilities. The power and data distribution component and the edge processing unit are designed to fit within, or adjacent to, standard electrical wall boxes or low-voltage enclosures commonly used for power receptacles and structured cabling. As a result, installation may be performed by electricians or facilities personnel familiar with conventional power and wired network installation, without requiring specialized information technology or medical device integration expertise.

Medical devices present in the room are integrated independently by attaching a corresponding device-interface module to each device. This per-device attachment model avoids the need for room-level protocol configuration, device aggregation, or custom network engineering. Each device-interface module is physically connected to its associated medical device and to the wall-mounted infrastructure using standardized cabling, allowing device integration to be performed incrementally as devices are introduced, replaced, or reassigned.

Once physically installed, the infrastructure components automatically enroll and coordinate under control of the edge processing unit, applying predefined templates and governance policies without manual configuration at the bedside. The retrofit deployment model therefore allows existing care environments to be upgraded using standardized installation practices and non-specialist labor, while producing a secure, governed medical device integration plane suitable for downstream monitoring, documentation, analytics, and artificial intelligence systems.

Figures 7, 7A, 7B, 7C, 7D, 7E, 7F, 7G:
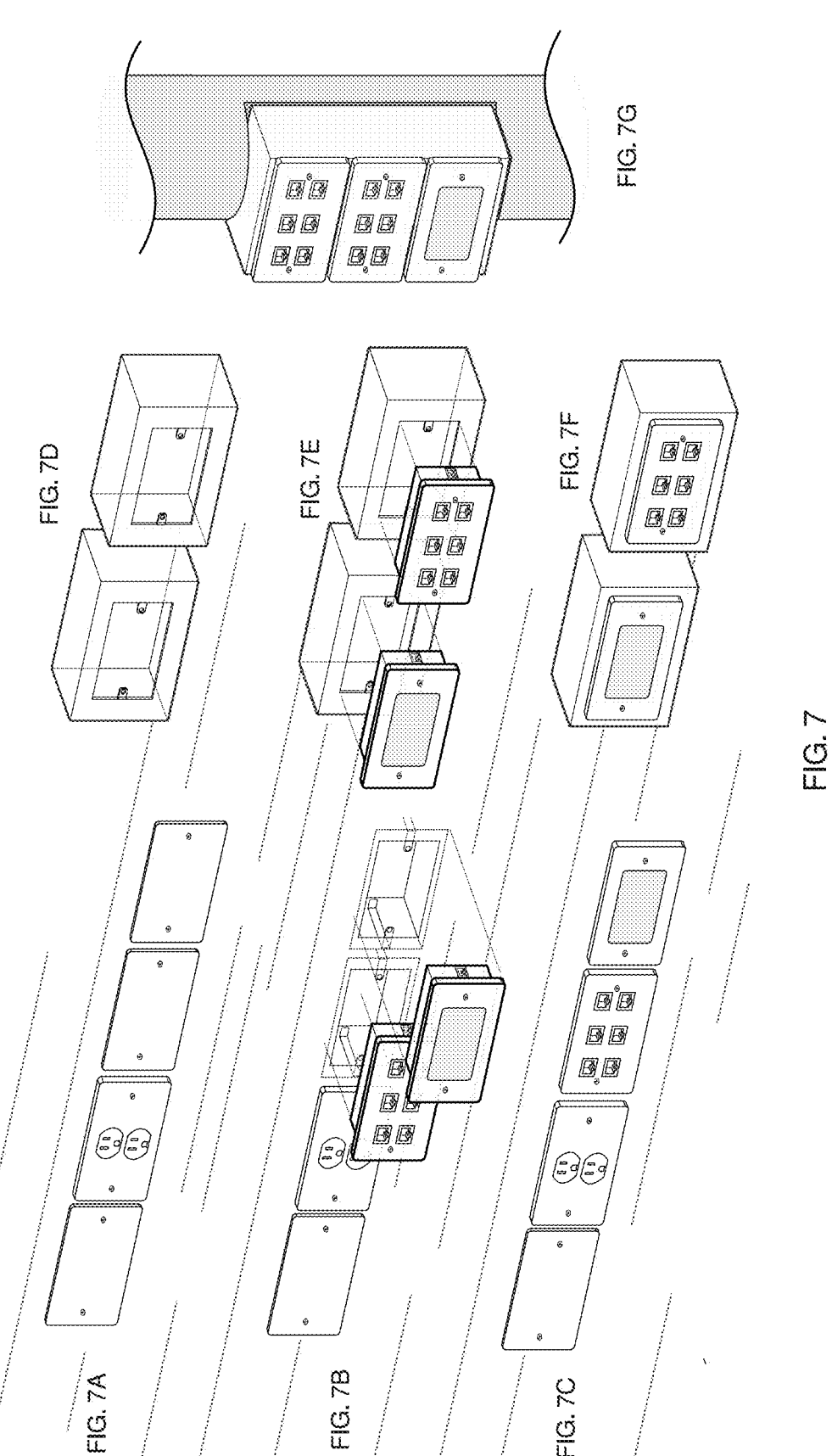
FIG. 7 shows a non-limiting example of retrofit deployment using existing bedside wall locations within a healthcare facility, illustrating installation of clinical integration nodes at locations associated with electrical outlets, switches, or low-voltage terminations, as well as surface-mounted and pole-mounted installations that do not require structural renovation.

FIG. 7 illustrates exemplary retrofit arrangements in which wall-mounted clinical integration nodes are installed at locations previously occupied by standard wall plates, thereby leveraging existing wall cavities and electrical infrastructure without structural renovation.

Template-Based Configuration

A room or area template may include one or more of expected device roles and device types for a legacy room type, allowable interfaces and protocols for each role, mappings between labeled network drops, physical mount points, QR or barcode identifiers, and location identifiers, default routing rules indicating destinations for standardized data objects, default security policies including enrollment authentication requirements and transport encryption settings, and validation rules for detecting configuration anomalies, such as a missing required device role or a duplicated role assignment within a room.

Worked Example: Retrofit of a Legacy ICU Wing

As an illustrative example, a hospital may retrofit a legacy intensive care unit wing comprising a plurality of rooms by deploying pre-assembled retrofit packages. For each room, a technician mounts device-interface modules to existing IV poles or equipment rails, connects modules to legacy devices using vendor-specific cables, and installs wall-mounted or in-wall infrastructure components using existing power outlets and existing network drops. The technician applies an ICU room template to a set of rooms, causing enrolled modules to receive location identifiers, default device roles, and routing rules. During operation, if network connectivity is disrupted for a period of time, standardized data objects are buffered at the edge and replayed when connectivity returns. If two monitors are swapped between beds, the system updates device-to-location associations based on enrollment and template rules to reduce mis-assignment of data. In coexistence mode, legacy devices continue to communicate with vendor-specific intermediary devices over existing primary paths while the system obtains a parallel copy of device outputs for downstream governance and AI systems.

System Architecture

The retrofit medical device integration infrastructure disclosed herein is implemented as a coordinated physical and logical system comprising three primary components that together establish a controlled clinical integration plane within an existing healthcare facility. These components are: a device-interface module configured to couple directly to an individual medical device; a wall-mounted or in-wall power and data distribution component configured to serve as a local utility hub; and a wall-mounted or in-wall edge processing component configured to act as the network authority for the integration plane. The architecture is expressly designed so that these components may be installed using existing building services and operate independently of the hospital's general IT network while remaining interoperable with downstream clinical systems.

At the edge of the system, a device-interface module is physically and logically coupled to a medical device at or near the point of care. The device-interface module is configured to receive device output data using a device-specific physical connector and protocol processing logic appropriate to the particular device model and software configuration. The module operates as an acquisition point for device data, obtaining outputs in a manner that does not require modification of the medical device and does not interfere with any incumbent primary communication pathway used by the device. In embodiments supporting coexistence, the device-interface module may include a pass-through or parallel connection that allows the medical device to continue communicating with an existing vendor-specific intermediary device or central station while simultaneously providing a copy of device outputs to the disclosed infrastructure.

One or more device-interface modules are coupled via standardized cabling to a wall-mounted or in-wall power-over-ethernet distribution component. This distribution component provides electrical power and data connectivity to the device-interface modules using a controlled and isolated network segment dedicated to medical device integration. Unlike general-purpose network switches, the distribution component is configured to operate under exclusive control of the edge processing component and does not provide unrestricted access to the hospital's wired network. By physically locating the distribution component at or near an existing electrical outlet location, the architecture leverages ubiquitous bedside anchor points while minimizing exposed cabling and reducing risk of accidental disconnection or interference in patient care areas.

The edge processing component is coupled to one or more distribution components and serves as the central authority for the clinical integration plane. The edge processing component performs device discovery, authentication, and authorization, and establishes the logical isolation boundary that separates the integration plane from the hospital's general IT infrastructure. All data entering or leaving the integration plane passes through the edge processing component, which applies security policies, time alignment, buffering, logging, and routing functions. In this manner, the edge processing component enforces hospital-defined governance controls at the network layer, rather than relying on device vendors or downstream systems to impose such controls.

In operation, when a device-interface module is connected to a distribution component, the edge processing component automatically detects the connection and validates the identity and authorization status of the module. Upon successful authorization, the edge processing component associates the module with a physical location derived from the connection point, room template, or installation context, and may further associate the module with a patient identifier obtained through integration with admission, discharge, and transfer systems. Device output data acquired by the module is then normalized into a standardized format and encapsulated into governance-ready data objects that include identity, location, and time information. These data objects are buffered and routed by the edge processing component to designated downstream destinations using secure and controlled transport mechanisms.

The architecture is modular and scalable. Multiple distribution components may be deployed within a room, bay, or clinical area and may be managed by a single edge processing component. Additional device-interface modules may be added incrementally as new devices are introduced, without reconfiguration of existing modules or changes to the physical infrastructure. Similarly, additional edge processing components may be deployed to increase capacity or to serve additional rooms or units, while maintaining consistent governance and security policies across the integration plane.

Importantly, the system architecture does not require that downstream systems be aware of the specific devices or protocols present at the bedside. By presenting standardized, context-aligned data objects at the output of the integration plane, the architecture decouples bedside device heterogeneity from downstream monitoring, documentation, analytics, and artificial intelligence systems. This decoupling allows hospitals to evolve device inventories and downstream software independently, while maintaining consistent integration behavior at the infrastructure level.

As used herein, delivery of power "over Ethernet" or "power-over-Ethernet" refers to the functional concept of supplying electrical power to connected devices over a wired data communication cable, such as Ethernet cabling, and is not limited to any specific commercial product implementation, vendor, or formal power delivery standard. The disclosed infrastructure may employ standardized, proprietary, or hybrid power delivery techniques over data cabling, provided that such techniques enable combined power and data connectivity suitable for the described retrofit deployment.

The described architecture therefore establishes a durable, repeatable foundation for retrofit medical device integration. By fixing the roles of the device-interface module, the wall-mounted distribution component, and the edge processing component, the system defines a concrete infrastructure that can be installed, audited, licensed, and enforced as a unit, while supporting incremental expansion and future functional extensions through downstream systems or subsequent patent continuations.

Connection Event Detection, Authorization, and Enrollment Workflow

Upon physical connection of a device-interface module to a powered connection port of a distribution component, the edge processing unit detects a connection event corresponding to that specific port identity. Detection may occur based on electrical presence, link-layer signaling, or other physical-layer indicators associated with the powered connection port. In response to the connection event, the edge processing unit initiates an authentication process to determine whether the connected device-interface module is authorized to participate in the clinical integration plane.

Authentication includes verification of one or more identifiers associated with the device-interface module, including a module identifier, firmware signature, or cryptographic credential. In some embodiments, mutual authentication is performed between the device-interface module and the edge processing unit prior to acceptance of any device output data. If authentication succeeds, the edge processing unit applies applicable governance and routing policies and authorizes the device-interface module for operation within the clinical integration plane.

Upon authorization, the edge processing unit assigns a physical location identifier to the device-interface module based at least in part on the identity of the powered connection port to which the module is connected. The edge processing unit then enables data ingress from the module and generates standardized data objects from normalized device output data, each standardized data object including device identity information, assigned location information, and time information. The connection event, authorization result, assigned location, and time of activation are recorded in an audit log.

If authentication fails, the edge processing unit places the device-interface module into a quarantine state in which power delivery and/or data ingress is disabled or restricted. If a device-interface module is unknown or unrecognized, the edge processing unit may permit limited operation in a safe mode that prevents routing of device data to downstream systems until explicit authorization is obtained. In all cases, unauthorized or quarantined modules are prevented from introducing data into the clinical integration plane.

Structural Enforcement of Security and Isolation Boundaries

Security within the disclosed infrastructure is enforced as a structural property of the clinical integration plane. In some embodiments, device-interface modules and edge processing units implement secure boot mechanisms and execute signed firmware or driver bundles. Mutual authentication is performed between device-interface modules, distribution components, and edge processing units prior to acceptance of device data.

Cryptographic keys are managed using a centralized or distributed key management model appropriate to the deployment. Unauthorized modules are placed into quarantine states in which power delivery and data ingress are restricted. All authorization, association, and routing events are recorded in audit logs, which may be stored in a tamper-evident form.

Medical devices and device-interface modules are prevented from obtaining direct connectivity to the general hospital information technology network. All communication with downstream systems occurs through controlled, authenticated, and authorized pathways mediated by the edge processing unit, thereby enforcing isolation and governance at the point of acquisition rather than relying on downstream controls.

Security and Integrity at Acquisition

In some embodiments, an integration module authenticates to a configuration service or management endpoint using one or more of device certificates, cryptographic keys, or credentialed enrollment procedures. Standardized data objects may be encrypted in transit from the point of acquisition. In addition, the system may bind a device identifier to an enrolled module identifier and a location identifier to reduce spoofing or unauthorized substitution. In some embodiments, a standardized data object includes a cryptographic hash or signature over at least a portion of the object to support downstream integrity checking, without requiring modification of the legacy medical device.

Device-Interface Module (110): Device Interface and Coexistence

The Device-Interface Module (110) functions as a device-interface module configured to couple directly to an individual medical device at or near the point of care and to acquire device output data for entry into the retrofit integration infrastructure. Each Device-Interface Module is physically and logically adapted for use with a specific medical device model and configuration, and is designed to operate without requiring modification of the medical device or alteration of its certified operating state. The Device-Interface Module therefore serves as a controlled acquisition point for device data, rather than as a replacement for, or controller of, the medical device itself.

In some embodiments, the Device-Interface Module includes a device-specific physical connector that interfaces with a data export port of the medical device. Although such connectors may resemble standardized connectors such as RJ-type connectors, USB connectors, or Ethernet connectors, the internal wiring, signaling, and protocol handling are configured to match the specific electrical and logical characteristics of the target medical device. This device-specific adaptation allows the Device-Interface Module to receive device outputs accurately and reliably across a wide range of legacy and newly released medical equipment, including devices that do not natively support standardized data export formats.

The Device-Interface Module includes protocol processing logic configured to interpret device-specific output signals and to normalize those signals into a standardized internal representation suitable for further processing by the integration infrastructure. The Device-Interface Module does not perform clinical interpretation or diagnostic inference; rather, it performs deterministic translation and encapsulation of device outputs so that downstream components receive consistent, machine-consumable data structures regardless of device vendor or protocol. By performing this normalization at the point of acquisition, the infrastructure reduces downstream dependency on proprietary device formats and enables consistent governance and routing behavior across heterogeneous devices.

A practical requirement in retrofit environments is coexistence with incumbent vendor-specific intermediary devices and central monitoring systems that remain in clinical use. Accordingly, in some embodiments the Device-Interface Module is configured to support parallel data capture without interrupting the primary communication pathway used by the medical device. To this end, the Device-Interface Module may include a pass-through connector, inline adapter, or equivalent interface that allows the medical device to continue communicating with an existing vendor-specific intermediary device or central station while simultaneously providing a copy of the device output data to the disclosed infrastructure. The pass-through pathway preserves signal continuity and timing characteristics required by the incumbent system, while the parallel pathway supplies data to the hospital-owned integration plane.

In coexistence embodiments, the Device-Interface Module is configured so that the parallel capture function does not inject data into, alter, or delay the primary communication pathway. Electrical isolation, protocol isolation, and rate control mechanisms may be employed to ensure that operation of the Device-Interface Module does not interfere with incumbent monitoring workflows or violate device operating constraints. The selection of a particular capture mechanism—such as a pass-through connector, splitter, mirrored output, or protocol-level secondary export—is dependent on the characteristics of the medical device and is chosen to preserve safe and compliant operation.

The Device-Interface Module may be powered in multiple ways, including via power-over-ethernet supplied by the wall-mounted distribution component or via a low-voltage power interface provided by the medical device itself. When connected to the integration infrastructure via a controlled power-over-ethernet connection, the Device-Interface Module becomes part of the isolated clinical integration plane and is subject to authorization and control by the edge processing component. In such configurations, the physical connection point may be used as an input to location association logic, enabling the infrastructure to determine the bed, room, or care area with which the Device-Interface Module is associated.

In operation, when an Device-Interface Module is connected to the integration infrastructure, it is automatically discovered by the edge processing component, authenticated, and authorized before any device data is accepted. The Device-Interface Module may present identifying information corresponding to its device-specific configuration, firmware version, and compatibility profile, allowing the edge processing component to verify that the Device-Interface Module is approved for use with the connected medical device. If authorization fails, the edge processing component may block data ingress from the Device-Interface Module, thereby preventing unauthorized or misconfigured devices from introducing data into the integration plane.

The Device-Interface Module is designed for rapid installation and removal in retrofit environments. In some embodiments, the Device-Interface Module is physically secured to the medical device using removable mounting mechanisms that do not interfere with routine clinical use, cleaning, or device servicing. This allows Device-Interface Modules to be deployed incrementally as devices are introduced or reassigned, and to be replaced or upgraded without altering the surrounding infrastructure.

By confining the responsibilities of the Device-Interface Module to device-specific data acquisition, normalization, and coexistence support, the disclosed architecture maintains a clear separation of concerns between bedside device interaction and downstream data governance. This separation allows the infrastructure to scale across large numbers of heterogeneous devices while preserving incumbent clinical workflows and avoiding tight coupling between device vendors and hospital-owned integration systems.

Wall-Mounted or in-Wall IoT Power-Over-Ethernet Switch (120)

The IoT Power-over-Ethernet Switch (120) functions as a dedicated power and data distribution component within the retrofit medical device integration infrastructure. The switch is configured to deliver electrical power and network connectivity to one or more device-interface modules using standardized Ethernet cabling, while maintaining a defined isolation boundary between medical device communications and the hospital's general information technology network. Unlike general-purpose enterprise switches, the IoT Power-over-Ethernet Switch is designed and deployed as a fixed clinical utility component rather than as a shared IT networking resource.

In retrofit embodiments, the IoT Power-over-Ethernet Switch is mounted on, within, or directly behind a wall at or near an existing electrical outlet location or low-voltage network termination point in a patient room, bay, or care area. The physical form factor and wiring interfaces of the switch are compatible with standard electrical wall boxes and low-voltage enclosures commonly used in healthcare facilities. This design allows installation to be performed using conventional electrical and structured-cabling practices by electricians or facilities personnel, without requiring specialized hospital IT or medical device integration expertise.

The IoT Power-over-Ethernet Switch provides multiple controlled ports, each port being configured to supply power and data connectivity to a corresponding device-interface module associated with an individual medical device. Power-over-Ethernet delivery enables both electrical power and network connectivity to be provided over a single cable, reducing cabling complexity and enabling clean, standardized bedside installation. Each port may be individually monitored and controlled by the edge processing unit, allowing device-level authorization, power management, and connectivity enforcement.

A defining characteristic of the IoT Power-over-Ethernet Switch is that it operates under the exclusive control of the IoT Edge Processing Unit and does not provide unrestricted network access. The switch is not configured to accept arbitrary network devices and does not function as a general access switch for hospital IT infrastructure. All communications through the switch are mediated by the edge processing unit, which authenticates connected device-interface modules, authorizes data ingress, and enforces isolation policies at the port level.

In some embodiments, the IoT Power-over-Ethernet Switch is electrically and logically isolated from other hospital networking equipment. Data traffic originating from connected device-interface modules is confined to the clinical integration plane and forwarded only through secure communication paths established and managed by the edge processing unit. This isolation prevents direct exposure of medical devices to the hospital's general network and reduces cybersecurity risk at the bedside.

The switch may further report operational status information, including port connectivity, power draw, and fault conditions, to the edge processing unit. In response to detected anomalies or unauthorized connections, the edge processing unit may disable a corresponding port, thereby suspending both power delivery and data flow until the condition is resolved. These controls support safe operation while enabling centralized oversight without bedside intervention.

Multiple IoT Power-over-Ethernet Switches may be deployed within a room, ward, or clinical area and managed by a single edge processing unit. Such switches may be interconnected through controlled uplinks that remain within the integration plane, allowing the infrastructure to scale to support additional medical devices without requiring changes to existing installations. Expansion is achieved by adding additional wall-mounted switches and device-interface modules using the same standardized installation practices.

By combining wall-mounted deployment, compatibility with standard electrical enclosures, controlled port behavior, and exclusive edge processing unit control, the IoT Power-over-Ethernet Switch establishes a durable and repeatable physical layer for retrofit medical device integration. This design enables hospitals to deploy governed, vendor-agnostic device connectivity using existing building infrastructure and non-specialist installation labor, while preserving clinical safety, security, and scalability.

IoT Edge Processing Unit (130)

The IoT Edge Processing Unit (130) functions as the central authority for the retrofit medical device integration infrastructure. It is a physically deployed computing component configured to manage authentication, authorization, isolation, governance, and routing within a clinical integration plane that is separate from the hospital's general information technology network. The IoT Edge Processing Unit enforces control at the network boundary and serves as the point through which all standardized medical device data entering or leaving the integration infrastructure is mediated.

In retrofit embodiments, the IoT Edge Processing Unit is mounted on, within, or directly behind a wall at or near existing electrical outlet locations or low-voltage network termination points within a patient room, ward, or care area. The physical form factor and power interfaces of the edge processing unit are compatible with standard electrical wall boxes or low-voltage enclosures commonly used in healthcare facilities. As a result, installation may be performed using conventional electrical and structured-cabling practices by electricians or facilities personnel, without requiring rack-mounted servers, dedicated data center space, or specialized hospital IT expertise.

The IoT Edge Processing Unit is electrically and logically coupled to one or more IoT Power-over-Ethernet Switches and operates as the exclusive controller of those switches. Upon physical connection of a device-interface module to a controlled switch port, the IoT Edge Processing Unit automatically detects the connection event and evaluates identifying information associated with the module. The edge processing unit authenticates and authorizes the module before permitting data ingress or power delivery, thereby preventing unauthorized or misconfigured devices from participating in the integration plane.

A core function of the IoT Edge Processing Unit is to enforce isolation and governance at the network layer. Medical devices connected through the infrastructure are not granted direct access to the hospital's general information technology network. Instead, all device data is routed through the edge processing unit using controlled, secure communication paths. Encryption, segmentation, and access control policies are applied at this boundary, ensuring that security and compliance controls are enforced at the point of acquisition rather than being deferred to downstream systems.

The IoT Edge Processing Unit further provides time alignment, buffering, and logging services for standardized data objects received from device-interface modules. In some embodiments, the unit maintains a synchronized time reference used to apply time information and sequence identifiers to incoming data. Local buffering allows continued acquisition of device outputs during upstream network interruptions, with ordered forwarding or replay once connectivity is restored. These functions support data integrity and auditability without requiring continuous availability of external systems.

In addition to routing and buffering, the IoT Edge Processing Unit maintains associations between device-interface modules, physical locations, and patient identifiers. Location association may be derived from the physical connection point or from applied room templates, while patient association may be obtained through integration with admission, discharge, and transfer systems. When devices are moved, swapped, or disconnected, the edge processing unit detects the change and updates the associated mappings, recording transition events with time information to prevent misattribution of device data.

The IoT Edge Processing Unit also serves as a centralized management and monitoring point for the retrofit infrastructure. It records authorization events, connectivity status, fault conditions, and anomalies associated with connected switches and device-interface modules. These records support troubleshooting, compliance auditing, and forensic analysis, while allowing day-to-day operation to proceed without manual configuration at the bedside.

Although the IoT Edge Processing Unit may include local computational resources capable of supporting optional downstream functions, such as data conditioning or aggregation, these capabilities are subordinate to its primary role as a network authority and governance enforcement point. The invention does not require execution of diagnostic inference, clinical decision-making, or therapeutic control at the edge processing unit, and such functions, if present, are performed by downstream systems outside the scope of the infrastructure itself.

By providing a wall-mounted, electrician-installable network authority that enforces isolation, governance, attribution, and secure routing, the IoT Edge Processing Unit enables scalable retrofit deployment of medical device integration infrastructure using existing building services. This design allows hospitals to establish a governed, standardized integration plane without reliance on specialized IT installations or device-specific configuration at the point of care.

Time Synchronization, Buffering, and Ordered Replay

To maintain continuity of governed data capture during network disruptions, the edge processing unit includes local buffering capability. Standardized data objects received from authorized device-interface modules are stored in a buffer structure, such as a queue or ring buffer, together with time information and sequence identifiers. Time information may be derived from a synchronized time source and includes sufficient resolution to preserve ordering of clinical events.

If upstream connectivity to a downstream system is interrupted, standardized data objects continue to be buffered locally. Upon restoration of connectivity, buffered data objects are forwarded in time order based on sequence identifiers and timestamps. In some embodiments, deduplication logic is applied to prevent retransmission of data objects that were successfully delivered prior to interruption.

In some embodiments, freshness policies are applied to buffered data. Data objects exceeding a defined age threshold may be marked as stale or excluded from replay, while still being retained for audit purposes. Time synchronization is maintained using one or more time sources, and drift is detected and corrected by the edge processing unit to preserve ordering integrity.

Autodiscovery, Location, and Patient Association

Accurate association between medical devices, physical location, and patient identity is a fundamental requirement for safe and reliable medical device integration, particularly in retrofit environments where devices are frequently moved, swapped, or shared across beds and rooms. The disclosed infrastructure addresses this requirement by implementing automated discovery and association mechanisms that operate at the time of physical connection and that are enforced by the edge processing component, rather than relying on manual configuration or downstream reconciliation.

In the disclosed architecture, device-interface modules are automatically detected by the IoT Edge Processing Unit when they are physically connected to a controlled port of an IoT Power-over-Ethernet Switch. The connection event itself serves as a trigger for discovery and enrollment, allowing the infrastructure to determine that a specific, authorized device-interface module has been introduced into the integration plane. This discovery process does not require manual entry of device identifiers or network configuration parameters at the bedside.

Location association is derived from the physical connection context of the device-interface module. In some embodiments, each controlled switch port is pre-associated with a room, bed, bay, or care area identifier using a predefined template or configuration service. When a device-interface module is connected to a particular port, the IoT Edge Processing Unit assigns the corresponding location identifier to the module and to the standardized data objects produced from its acquired device outputs. Because location is inferred from the physical infrastructure rather than from device-reported metadata, the association remains consistent even when devices are swapped, replaced, or temporarily disconnected.

Patient association may be established by correlating the assigned location identifier with patient occupancy information obtained from admission, discharge, and transfer systems. In such embodiments, the IoT Edge Processing Unit determines which patient is currently assigned to the associated bed or care area and links the standardized device data objects to the corresponding patient identifier. This association may be updated dynamically as patient assignments change, without requiring reconfiguration of the device-interface module or modification of the medical device itself.

The infrastructure is configured to detect and respond to changes in device placement or connectivity. When a device-interface module is disconnected from one controlled port and later connected to a different port, the IoT Edge Processing Unit treats the event as a relocation and updates the associated location and patient mappings accordingly. Transition events are logged with time information, enabling reconstruction of device movement history and supporting auditability of downstream data usage. By updating associations at the time of physical reconnection, the system reduces the risk of false patient-device attribution that can occur when devices are moved between beds during routine clinical operations.

In some embodiments, the IoT Edge Processing Unit applies validation logic to detect unexpected or inconsistent configurations, such as a device appearing in a location where it is not expected based on the applied room template or a device type being connected to an incompatible care area. Such conditions may be logged, flagged for review, or temporarily blocked from data ingress until resolved, thereby preventing erroneous data associations from propagating to downstream systems.

The automated association mechanisms described herein operate independently of downstream monitoring, documentation, or analytics systems. Standardized data objects emitted by the integration plane include the assigned device, location, and patient identifiers, allowing downstream systems to consume correctly attributed data without performing their own reconciliation. This separation of concerns simplifies downstream system design and places responsibility for attribution correctness within the infrastructure itself, where physical context is directly observable.

By grounding discovery and association in physical connection events and controlled infrastructure ports, the disclosed system provides a repeatable and verifiable method for maintaining correct device-location-patient mappings in retrofit environments. This approach reduces reliance on manual labeling, barcode scanning, or user intervention at the bedside, and supports scalable deployment across large numbers of heterogeneous rooms while preserving auditability and governance.

Port-Based Location Binding and Device Movement Handling

Location association within the clinical integration plane is anchored to physical port identity rather than to device-reported metadata. Each powered connection port of a distribution component is associated with a location identifier corresponding to a bed, bay, room, or care area. When a device-interface module is connected to a port, the assigned location identifier is derived from that port identity and persists for the duration of the connection.

If a device-interface module is disconnected from a first powered connection port and subsequently connected to a second powered connection port, the edge processing unit detects the disconnection and reconnection events and treats the change as a physical relocation. The assigned location identifier is updated based on the second port identity, and a transition event including the prior location, new location, and time information is recorded. Standardized data objects generated after reconnection include the updated location information.

In a representative example, if two bedside monitors are swapped between beds, the device-interface modules are disconnected and reconnected to different ports. The edge processing unit updates location associations automatically based on port identity, without requiring manual relabeling or reconfiguration, thereby preventing misattribution of device data to the wrong patient. If ambiguity arises, such as simultaneous connection events or conflicting identifiers, the edge processing unit may temporarily hold data in a pending state and issue an alert until the association is resolved.

In some embodiments, additional signals such as admission-discharge-transfer events, enrollment scans, or contextual confirmation inputs may be used to validate or refine associations. All association changes are logged with time information to support auditability and reconstruction of device movement history.

Coexistence with Legacy Vendor-Specific Intermediary Devices

Healthcare facilities commonly rely on vendor-specific intermediary devices, bedside networks, and central monitoring stations that are tightly integrated into existing clinical workflows and contractual service arrangements. In many cases, these incumbent systems cannot be removed, replaced, or substantially reconfigured without disrupting patient care, invalidating warranties, or requiring extensive regulatory and operational approvals. The disclosed retrofit medical device integration infrastructure is therefore designed to operate alongside such incumbent systems rather than in place of them.

In coexistence embodiments, the disclosed infrastructure acquires device output data without interrupting or altering the primary communication pathway used by a medical device to communicate with an existing vendor-specific intermediary device or central station. A device-interface module may be coupled to the medical device in a manner that allows the device to continue transmitting data to the incumbent system while simultaneously providing a parallel copy of the same outputs to the hospital-owned integration plane. The incumbent pathway remains functionally unchanged, and the disclosed infrastructure does not assume responsibility for primary patient monitoring or alarm delivery performed by the vendor system.

Parallel data capture may be implemented using a variety of non-intrusive mechanisms selected based on the characteristics of the medical device and the incumbent system. In some embodiments, the device-interface module includes a pass-through connector or inline adapter that relays device signals to the vendor-specific intermediary devices while exposing a secondary output for capture. In other embodiments, signal duplication may be achieved using a splitter, mirrored port, or protocol-level secondary export stream, where such mechanisms are supported by the device or vendor-specific intermediary device. Regardless of the capture mechanism, the disclosed infrastructure is configured to preserve the timing, electrical characteristics, and protocol behavior of the primary pathway. Examples include inline pass-through connectors, Y-splitter cables, relay-based splitters, port mirroring at a distribution component, network taps, or equivalent arrangements that preserve the timing, electrical characteristics, and protocol behavior of the primary communication pathway.

To ensure safe coexistence, the disclosed infrastructure enforces isolation between the parallel capture pathway and the incumbent vendor pathway. Electrical isolation, protocol isolation, and rate control mechanisms may be employed to prevent backflow, signal injection, or interference with the primary communication channel. The device-interface module and downstream components operate in a receive-only or observation mode with respect to the captured device outputs, such that no commands, configuration changes, or control signals are transmitted to the medical device via the parallel pathway.

The standardized data objects produced from the parallel capture stream are routed exclusively through the hospital-owned integration plane and are subject to governance controls imposed by the IoT Edge Processing Unit. These outputs may be delivered to downstream monitoring, documentation, analytics, or artificial intelligence systems independently of the incumbent vendor system. By decoupling parallel data capture from incumbent monitoring workflows, the disclosed infrastructure enables hospitals to introduce governed, standardized data flows incrementally, without destabilizing existing clinical operations.

In some embodiments, the IoT Edge Processing Unit monitors the health of the parallel capture pathway and the status of the device-interface module. If a fault, disconnection, or anomaly is detected, the infrastructure may log the event and suspend ingestion from the affected module without affecting the primary communication pathway. This behavior ensures that failures within the retrofit infrastructure do not propagate to incumbent systems relied upon for patient safety.

The coexistence capability further supports phased deployment across a facility. Hospitals may selectively retrofit rooms, beds, or device types while leaving other areas unchanged, allowing gradual adoption and validation. Because the disclosed infrastructure does not require exclusive access to medical devices or replacement of vendor-specific intermediary devices, coexistence embodiments provide a practical path for hospital-wide deployment in environments characterized by heterogeneous equipment and long equipment lifecycles.

By explicitly supporting parallel operation with incumbent vendor-specific intermediary devices and central stations, the disclosed architecture addresses one of the principal barriers to retrofit medical device integration. The coexistence design enables hospitals to preserve existing investments and workflows while establishing a governed, standardized integration plane that can expand over time and support downstream innovation without forcing disruptive system replacement.

Parallel Data Capture Mechanisms and Non-Interference Guarantees

In coexistence embodiments, the disclosed infrastructure acquires a parallel copy of medical device output data while allowing the medical device to continue communicating with an incumbent vendor-specific intermediary device or monitoring system over its primary communication pathway. Parallel acquisition is implemented using non-intrusive mechanisms selected to preserve electrical safety, signal integrity, and protocol behavior of the primary pathway.

In some embodiments, a device-interface module includes a pass-through interface in which the primary device output is relayed unchanged to the incumbent vendor-specific intermediary device while a secondary copy is provided to the clinical integration plane. In other embodiments, parallel acquisition is achieved using a mirrored output, protocol-level export feed, or monitoring interface supported by the medical device or vendor monitoring system. In still other embodiments, signal duplication is performed using a tap or splitter that maintains electrical isolation between the primary and secondary paths.

In all coexistence configurations, failure or unavailability of the parallel acquisition path does not interrupt the primary communication pathway. If the parallel capture path fails, the device-interface module ceases data transmission to the clinical integration plane without affecting incumbent monitoring workflows. The edge processing unit may log the failure and suspend ingestion from the affected module while maintaining normal operation of the vendor system.

Template-Based Retrofit Configuration

Retrofitting existing healthcare facilities at scale requires a deployment model that minimizes reliance on per-room engineering, bespoke network configuration, or specialized technical expertise at the bedside. The disclosed infrastructure addresses this requirement through a template-based configuration approach that allows standardized deployment across heterogeneous rooms while preserving correct device attribution and governance.

In some embodiments, the system maintains one or more predefined configuration templates that describe expected characteristics of a room, bay, or care area. A template may specify, for example, a room identifier, expected device types or classes, logical bed positions, port-to-location mappings, and default governance or routing policies. Templates are created and managed centrally and are designed to be reused across multiple rooms with similar layouts or clinical functions, such as intensive care rooms, step-down units, or post-anesthesia bays.

During retrofit deployment, a technician or installer may associate a selected template with a physical room or care area. This association may be established prior to installation or at the time of installation using installation context, a configuration service, or a simple selection process. Once a template is applied, integration components installed in the room inherit the location identifiers, device role expectations, and policy parameters defined by the template, without requiring manual configuration of individual devices or network settings.

When a device-interface module is physically connected to a controlled port of an IoT Power-over-Ethernet Switch, the IoT Edge Processing Unit applies the active template to determine the module's location and role within the room. The module is then enrolled automatically, subject to authorization, and begins producing standardized data objects tagged with the appropriate contextual information. Because configuration is driven by the template rather than by manual input at the bedside, deployment can be performed by non-expert personnel using standardized installation practices, without requiring device-level protocol knowledge or specialized medical device integration expertise.

Template-based configuration further supports scalability and change management in retrofit environments. If a room layout or clinical function changes, a different template may be applied without modifying the physical infrastructure or reconfiguring individual devices. Similarly, if governance policies or routing rules are updated, the changes may be propagated centrally through the template mechanism, ensuring consistent behavior across all rooms to which the template applies.

The template approach also reduces the risk of configuration errors that can arise from ad hoc deployment or manual device labeling. By deriving location and role information from controlled infrastructure ports and predefined templates, the system avoids reliance on device-reported metadata or user-entered identifiers that may be inconsistent or incomplete. This improves reliability of downstream data attribution and supports auditability.

Importantly, the template-based configuration mechanism operates in conjunction with the physical retrofit infrastructure and does not require that downstream systems be aware of template details. Downstream consumers receive standardized, context-aligned data objects that already incorporate the appropriate identifiers and policies, allowing them to operate without knowledge of the specific room layouts or deployment variations present within the facility.

By enabling consistent, repeatable deployment without per-room customization, the template-based configuration mechanism allows medical device integration to be treated as a facilities-led infrastructure project rather than as a bespoke information technology integration effort. This distinction supports rapid retrofit deployment using existing building services and non-specialist installation labor, while maintaining a governed and scalable integration plane across the facility.

Resilient Transport and Optional Backhaul

The Device-Interface Module (110) functions as a device-interface module configured to be physically coupled to an individual medical device at or near the point of care. Each Device-Interface Module is dedicated to a single medical device and is designed to acquire output data directly from that device without requiring modification of the device's certified hardware, firmware, or clinical operation. This one-to-one pairing between a medical device and a corresponding Device-Interface Module allows devices to be integrated independently, without requiring room-level aggregation, protocol configuration, or specialized integration expertise.

In typical deployments, each medical device present in a care area is paired with its own dedicated Device-Interface Module. Integration is performed by physically attaching the appropriate Device-Interface Module to the medical device using a device-specific connector and connecting the Device-Interface Module to the wall-mounted infrastructure using standardized cabling. Because device-specific protocol handling is encapsulated within the Device-Interface Module itself, no device configuration, network configuration, or protocol mapping is required at the room or facility level. As a result, attachment of Device-Interface Modules to medical devices may be performed by clinical engineering or facilities personnel without requiring hospital IT staff or medical device integration specialists.

Each Device-Interface Module includes a device-specific physical connector configured to interface with a data export port of a corresponding medical device. Although such connectors may resemble standardized connectors, including RJ-type connectors, USB connectors, or Ethernet connectors, the internal wiring and signaling are adapted to match the electrical and logical characteristics of the target device. This device-specific adaptation enables accurate acquisition of device outputs across a wide range of legacy and newly released medical devices that may not share common communication standards.

The Device-Interface Module includes protocol processing logic configured to translate device-specific output signals into a standardized internal representation suitable for entry into the integration infrastructure. The Device-Interface Module performs deterministic acquisition and normalization of device outputs and does not perform diagnostic interpretation, clinical decision-making, or therapeutic control. By localizing device-specific protocol handling within the Device-Interface Module, the infrastructure avoids dependence on centralized middleware or per-room configuration and supports incremental deployment as devices are added or replaced.

In coexistence embodiments, the Device-Interface Module supports parallel data capture while preserving incumbent vendor communication pathways. The Device-Interface Module may include a pass-through connector or inline interface that allows the medical device to continue communicating with an existing vendor-specific intermediary device or central monitoring system while simultaneously providing a parallel copy of the device output data to the hospital-owned integration plane. The primary communication pathway remains unchanged, and the Device-Interface Module operates in a non-intrusive observation mode with respect to the medical device.

To ensure safe coexistence, the Device-Interface Module may implement electrical and protocol isolation between the primary communication pathway and the parallel capture pathway. Rate limiting, signal integrity preservation, and isolation mechanisms may be employed to prevent interference with incumbent systems. The Device-Interface Module does not inject commands or configuration changes into the medical device via the parallel pathway.

The Device-Interface Module may be powered either by a low-voltage power interface provided by the medical device or by power-over-ethernet supplied by the wall-mounted infrastructure. When powered via power-over-ethernet, the Device-Interface Module becomes part of the controlled clinical integration plane and is automatically discovered and authorized by the IoT Edge Processing Unit upon physical connection. The physical connection point is used as an input to location association, allowing the infrastructure to determine the bed, room, or care area with which the medical device is associated.

The Device-Interface Module is designed for rapid installation, removal, and replacement in retrofit environments. Secure but removable mounting mechanisms allow the Device-Interface Module to be attached to the medical device without interfering with routine clinical use, cleaning, or servicing. If a medical device is replaced or reassigned, the corresponding Device-Interface Module may be detached and a different device-specific Device-Interface Module attached without requiring changes to the wall-mounted infrastructure or downstream systems.

By enforcing a one-Device-Interface-Module-per-device integration model and encapsulating device-specific complexity within removable interface modules, the disclosed infrastructure enables medical devices to be connected using standardized installation practices and non-specialist labor. This approach supports scalable retrofit deployment, preserves incumbent vendor workflows, and establishes a consistent, governed data acquisition layer across heterogeneous device environments.

Backhaul Over Existing Electrical Wiring

In some embodiments, the clinical integration infrastructure includes an alternate backhaul path that utilizes existing facility electrical wiring to transport standardized data objects when conventional network connectivity is unavailable or insufficient. A receptacle module coupled to an electrical outlet communicates with a corresponding receiver or bridge module located at an aggregation point. Discovery and pairing between the modules are authenticated prior to data transport.

A secured communication path is established between the paired modules, the path being configured to protect data against unauthorized access, interception, or tampering. Link quality metrics including one or more of latency, throughput, error rate, or signal stability are continuously measured and compared against predefined transport criteria. The alternate backhaul is invoked as a fallback when a primary uplink is unavailable or degraded. Bandwidth prioritization rules are applied to ensure delivery of higher-priority clinical data classes.

If measured link quality metrics fall below a defined threshold, the system automatically transitions to an alternate uplink when available. Buffered data objects retain sequence and time integrity across the transition, and ordered replay behavior is preserved.

Mobile, Temporary, and Surge Deployments

In addition to deployment within fixed inpatient rooms, the disclosed retrofit medical device integration infrastructure is configured to support mobile, temporary, and surge care environments in which permanent installation is impractical or unavailable. Such environments may include transport settings, temporary wards, pop-up care areas, overflow units, or repurposed clinical spaces established in response to capacity surges or emergency conditions. The ability to extend the same integration plane to these settings further illustrates the infrastructure-centric nature of the invention.

In mobile and temporary deployments, the same device-interface modules, power and data distribution components, and edge processing components described herein may be mounted on carts, poles, rails, or other portable supports rather than being embedded in walls. These components may be coupled to available power sources and backhaul connections appropriate to the deployment context, including temporary electrical feeds, portable power supplies, or provisional network connections. Because the infrastructure relies on attach-on components and standardized interfaces, deployment does not require modification of the underlying building structure or installation of permanent fixtures.

The functional behavior of the integration infrastructure remains consistent across fixed and mobile deployments. Device-interface modules acquire device output data at the point of care, the edge processing component enforces authorization, isolation, and governance, and standardized data objects are produced and routed to designated downstream destinations. Location association in mobile deployments may be derived from the mounting context, assigned identifiers, or temporary templates rather than from fixed wall ports, but the association mechanism remains grounded in the physical deployment context rather than in manual data entry.

Mobile and temporary deployments may benefit from the resilient transport mechanisms described herein, including buffering, store-and-forward operation, wireless fallback, or optional mesh routing. These mechanisms allow the integration plane to remain operational even when conventional facility networking is unavailable, intermittent, or constrained. For example, a temporary surge unit may be instrumented with heterogeneous bedside devices connected through the integration infrastructure, with standardized data objects buffered locally and forwarded to a central processing location when connectivity permits.

In some embodiments, one or more device-interface modules may be deployed without a fixed wired connection to a bedside medical device and may instead operate as wireless-only integration nodes. As represented by reference numeral 116 in FIG. 6, such a module may be mounted to, integrated with, or otherwise associated with a patient bed, stretcher, chair, rail, or similar physical structure located within the care area, and may communicate with the integration infrastructure using a wireless communication link, including Wi-Fi and/or Bluetooth.

In these configurations, the device-interface module may acquire data that provides physical or environmental context relevant to interpretation of clinical measurements, without itself constituting a primary clinical measurement device. By way of example and not limitation, such contextual data may include bed position, inclination angle, posture state, movement, occupancy status, or other characteristics of the patient's immediate physical environment at the time clinical device data is generated.

Data acquired by such wireless-operating modules is treated as first-class input to the integration plane and is normalized, time-stamped, and encapsulated into standardized, governance-ready data objects under control of the IoT Edge Processing Unit. These data objects may be associated with a location identifier and, where applicable, with a patient identifier, and are subject to the same buffering, routing, authorization, and policy enforcement mechanisms as data acquired from primary medical devices.

Because the presence and connectivity of such modules are managed through the same discovery and enrollment processes as other infrastructure components, their operation may additionally support inference of asset presence or movement over time. Any such asset-related inference is secondary to, and incidental to, the infrastructure's primary function of governed data acquisition and does not require a separate tracking system or modification of clinical workflows.

Importantly, mobile and temporary deployments do not introduce new functional requirements beyond those of the core retrofit infrastructure. The same governance, security, and attribution controls apply, and downstream systems receive standardized, context-aligned data objects regardless of whether the data originated from a permanent room or a temporary care area. This consistency allows hospitals to extend existing monitoring, documentation, and analytics workflows to surge environments without introducing special-case integration logic.

When temporary deployments are no longer required, the integration components may be removed, relocated, or reassigned without leaving permanent alterations to the environment. This reversibility supports rapid response to changing clinical demands while preserving the integrity of the underlying facility. By enabling governed medical device integration in both permanent and temporary settings using the same architectural components, the disclosed invention provides a flexible yet unified approach to retrofit deployment across diverse care scenarios.

Core Retrofit Architecture and Clinical Integration Spine

The disclosed system is organized around a core clinical integration spine that distinguishes it from conventional intermediary devices, middleware platforms, or vendor-specific monitoring systems. This spine defines a physical and logical infrastructure that operates as a hospital utility layer rather than as a device-dependent interface.

First, the infrastructure is deployed as a retrofit installation at existing bedside wall locations, including electrical outlet positions and low-voltage wall plates, using standard wall boxes or surface-mounted enclosures already present in the facility. This deployment model enables installation without structural renovation and without removal or replacement of incumbent medical devices.

Second, the infrastructure establishes a controlled clinical integration plane that is structurally and logically isolated from the hospital's general information technology network. Medical devices and device-interface modules do not obtain unrestricted network access; instead, all ingress and egress of device data is mediated by an edge processing unit that enforces authorization, isolation, and governance at the network boundary.

Third, the architecture explicitly supports coexistence with incumbent vendor monitoring pathways. Medical devices may continue to communicate with third-party or incumbent vendor monitoring system or central stations over their existing primary communication paths, while the disclosed infrastructure obtains a parallel copy of device outputs through non-intrusive interfaces. This coexistence capability preserves clinical workflows, warranties, and regulatory status while enabling hospital-owned data acquisition.

Fourth, device outputs acquired within the clinical integration plane are normalized into standardized data objects that include, at minimum, device identity, physical location association derived from the infrastructure connection point, and time information. Location binding is anchored to controlled ports and physical installation context rather than to device-reported metadata, enabling reliable attribution during device moves, swaps, or reassignment events.

Together, these elements define a retrofit-deployable clinical utility plane that is distinct from conventional intermediary devices or middleware solutions. The infrastructure provides governed, location-aware, and time-aligned medical device data as a foundational service upon which downstream monitoring, documentation, analytics, and artificial intelligence systems may operate.

The clinical integration spine operates as a physical and logical infrastructure layer and does not itself perform clinical reasoning or medical decision-making, but instead supplies standardized, attributed, and governed data inputs to downstream systems that may perform such functions independently.

Technical Effects and Implementation Outcomes

The retrofit architecture described herein produces technical effects that are not achieved by conventional medical device intermediary devices or by generic enterprise networking practices applied at the bedside. By anchoring deployment to existing bedside wall locations and standard enclosures already present in the facility, the infrastructure reduces installation complexity and enables deployment on a facilities-led timeline, including rapid upgrade of legacy rooms without wall demolition, new conduit installation, or per-room network engineering. In practical deployment scenarios, the same room-agnostic installation pattern can be repeated across many rooms using standardized mounting and cabling practices, thereby reducing reliance on specialist integrators and minimizing clinical downtime.

The controlled clinical integration plane further produces a cybersecurity and safety effect by preventing bedside devices and device-interface modules from obtaining direct connectivity to the hospital's general information technology network. Instead of extending unmanaged network access to heterogeneous devices, all ingress and egress of device data is mediated by the edge processing unit, which enforces authorization and routing at the boundary of the plane. This structural isolation reduces the attack surface associated with exposing legacy devices to enterprise networks and provides a consistent enforcement point for governance and transport controls independent of device vendor capabilities.

A further technical effect of the disclosed architecture is improved attribution correctness during routine clinical operations in which devices are moved, swapped, or temporarily disconnected. Because location association is derived from controlled infrastructure connection context and port identity rather than device-reported metadata, the system reduces misattribution risk when two devices are exchanged between beds or when a device-interface module is reconnected at a different location. The infrastructure further supports continuity of governed data acquisition during upstream network interruptions by buffering standardized data objects locally. In some embodiments, buffered standardized data objects may be forwarded in an ordering-consistent manner based on one or more ordering indicators, such as timestamps and/or sequence markers, to preserve ordering continuity across intermittent connectivity conditions.

In coexistence embodiments, an additional technical effect is achieved by obtaining a parallel copy of device outputs while allowing incumbent vendor monitoring pathways to remain primary and uninterrupted. This permits incremental retrofit deployment without destabilizing established clinical workflows, without requiring replacement of incumbent vendor systems, and without requiring downstream systems to implement device-specific protocol handling. The practical result is a retrofit-deployable hospital utility plane that provides governed, location-aware, and time-aligned device data objects as a foundational service for downstream monitoring, documentation, analytics, and computational systems.

The designation of the infrastructure as "AI-ready" reflects the quality and governance of the standardized outputs produced by the clinical integration plane, rather than the execution of artificial intelligence within the infrastructure itself.

Implementation Constraints in Clinical Environments and Rationale for the Architecture Clinical environments impose constraints that materially differ from ordinary enterprise networking and general-purpose IoT deployments. Bedside areas commonly contain heterogeneous and long-lived devices whose network behavior, patch cadence, and security capabilities are not controlled by the facility, and hospitals typically restrict unmanaged network media and ad hoc switching at the bedside due to safety, availability, and cybersecurity concerns. As a result, approaches that merely connect devices to the hospital's general information technology network, or that rely on per-room bespoke integration work, are operationally disfavored and can introduce unacceptable risk of downtime, misconfiguration, or device exposure.

In addition, incumbent vendor monitoring pathways and vendor-specific intermediary devices are frequently treated as primary clinical infrastructure and may be tightly coupled to established workflows, service agreements, and regulatory validation practices. These realities create friction against overlay systems that require replacing, reconfiguring, or interrupting vendor pathways, even when additional downstream data feeds are desired. A naïve attempt to add an auxiliary data feed by inserting uncontrolled adapters, unmanaged Wi-Fi bridges, or generic middleware may fail to preserve non-interference with incumbent systems, may not maintain correct device-location association during routine moves, and may not provide continuity when network conditions degrade.

The disclosed architecture addresses these constraints by establishing a controlled clinical integration plane that is physically deployable in retrofit form and that enforces authorization, isolation, and governed routing at the point of acquisition. Coexistence mechanisms allow the incumbent vendor pathway to remain primary while the hospital-owned plane acquires a parallel copy of device outputs without affecting primary operation. Port-identity-based location binding anchors attribution to the facility-controlled infrastructure connection context rather than to device-reported metadata, thereby improving correctness under swaps and moves. Time alignment, buffering, and ordered forwarding further provide continuity properties that are not inherent to generic network attachments. In this way, the disclosed system implements a practical and technically constrained solution tailored to the realities of bedside deployment in legacy facilities.

Medical Device Information Exchange (MDIX) Concept

The retrofit medical device integration infrastructure described herein may be understood, at a conceptual level, as providing a medical device information exchange within a healthcare facility. This exchange operates at the level of medical device data acquisition and normalization, and is distinct from vendor-specific intermediary devices, central monitoring stations, or downstream clinical applications. Its primary role is to provide a neutral, hospital-owned layer through which heterogeneous medical device outputs can be acquired, standardized, attributed, and governed before being consumed by downstream systems.

In conventional clinical environments, medical device data flows are typically constrained within vendor-specific ecosystems, with each manufacturer providing its own vendor-specific intermediary devices, proprietary formats, and central systems. As a result, data exchange across devices from different vendors often requires bespoke interfaces, middleware layers, or manual reconciliation. In contrast, the disclosed infrastructure establishes a common integration plane in which device outputs are acquired at the point of care, normalized into standardized data objects, and made available for downstream use under hospital-defined governance controls. This allows downstream systems to consume device data without requiring direct coupling to device-specific protocols or vendor-defined communication paths.

The medical device information exchange provided by the disclosed infrastructure is analogous, in function, to health information exchanges used for electronic medical records, but operates at the level of real-time and near-real-time medical device data rather than at the level of clinical documentation. The exchange does not store or curate medical records, nor does it replace downstream monitoring, documentation, or analytics systems. Instead, it provides a standardized and governed interface through which device data may be accessed by such systems in a consistent and auditable manner.

Importantly, the medical device information exchange is implemented as part of the physical retrofit infrastructure rather than as a purely software-based service. Device-interface modules, controlled power and data distribution components, and edge processing units cooperate to enforce isolation, authorization, attribution, and transport policies at the network layer. This architectural choice allows the exchange to be deployed incrementally using existing building services and attach-on components, and ensures that governance controls are applied at the point of acquisition rather than being deferred to downstream systems.

The exchange is neutral with respect to device manufacturers and downstream consumers. It does not require that devices conform to a single vendor ecosystem, nor does it impose assumptions about how downstream systems visualize, analyze, or act upon the standardized data objects it produces. By decoupling device heterogeneity from downstream system design, the medical device information exchange enables hospitals to evolve both device inventories and software platforms over time while preserving a stable integration foundation.

The medical device information exchange described herein is enabled by the retrofit integration infrastructure and is not dependent on any particular downstream application, analytics engine, or artificial intelligence system. Its function is to provide governed, standardized access to medical device data as an infrastructure capability, upon which diverse clinical and operational workflows may be built without requiring changes to the underlying physical deployment.

Vendor Compatibility and Downstream Interoperability

The retrofit medical device integration infrastructure described herein is configured to support downstream interoperability by producing standardized, governance-ready data objects that are decoupled from device-specific communication protocols and vendor-defined data formats. This design allows medical device data acquired at the point of care to be consumed by heterogeneous downstream systems without requiring such systems to establish direct connectivity to the originating medical devices or to implement device-specific protocol handling.

In some embodiments, standardized data objects generated by the infrastructure may be adapted for delivery to electronic medical record systems, clinical documentation platforms, monitoring systems, analytics services, or other downstream applications that rely on structured healthcare data exchange. Such adaptation may include transformation of standardized data objects into representations compatible with healthcare data exchange frameworks commonly employed by electronic medical record systems, including message-based or resource-based interfaces, while preserving device identity, location context, time information, and provenance metadata. These adaptations occur downstream of the device-interface modules and do not require modification of the physical deployment, device-specific acquisition logic, or bedside installation.

The infrastructure is configured to support concurrent delivery of standardized data objects to multiple downstream systems operating independently of one another. In some embodiments, one downstream system may apply data governance, validation, and policy enforcement functions, while another downstream system may perform remote monitoring or visualization functions. Each downstream system operates within its own logical execution environment and receives data through an isolated communication path, such that operation of one downstream system does not interfere with, constrain, or depend upon operation of another. The retrofit integration infrastructure does not assume responsibility for the internal behavior of downstream systems and does not require that such systems share a common execution environment.

Importantly, the disclosed infrastructure does not require replacement of incumbent vendor-specific intermediary devices, central monitoring stations, or proprietary vendor workflows. In coexistence embodiments, vendor-specific systems may continue to operate using their existing primary communication pathways, while standardized data objects produced by the hospital-owned integration plane are delivered independently to other downstream consumers. The infrastructure therefore enables interoperability across vendor ecosystems without asserting functional equivalence to, or behavioral emulation of, vendor-specific central stations.

The role of the infrastructure with respect to downstream interoperability is limited to acquisition, normalization, attribution, and governed transport of medical device data. The infrastructure does not perform clinical interpretation, diagnostic inference, alarm management, visualization, or therapeutic decision-making. Any such functions are performed exclusively by downstream systems operating outside the scope of the retrofit integration infrastructure.

By separating device acquisition and normalization from downstream consumption and by enforcing governance controls at the network boundary, the disclosed architecture establishes a stable and extensible integration foundation. This foundation allows downstream systems to evolve, be replaced, or be introduced incrementally over time without requiring changes to the physical deployment, device-interface modules, or installation practices, thereby supporting long equipment lifecycles and heterogeneous vendor environments common in healthcare facilities.

Infrastructure as Extension Interface

In some embodiments, the retrofit medical device integration infrastructure may function as a standardized extension interface through which additional data sources can be associated with an existing medical device or care context. This extension capability is implemented at the infrastructure level and operates by aggregating and contextualizing multiple data streams, rather than by modifying, controlling, or extending the certified functionality of any individual medical device.

In such embodiments, one or more additional data sources may be coupled to the infrastructure through device-interface modules or other authorized attachment points. These data sources may include, for example, auxiliary physiologic sensors, environmental sensors, wearable devices, or third-party measurement instruments that are not natively integrated into a primary bedside device. The infrastructure acquires outputs from these sources using device-appropriate interfaces and normalizes the outputs into standardized data objects in the same manner as for primary medical devices.

The standardized data objects produced from additional data sources may be associated, by the IoT Edge Processing Unit, with a corresponding medical device, physical location, or patient identifier based on deployment context and configuration. This association allows downstream systems to receive a coherent and time-aligned view of multiple related data streams without requiring that the primary medical device be modified or that its certified software or hardware be altered. The infrastructure therefore operates as an aggregation and association layer rather than as a functional extension of the medical device itself.

Importantly, the extension interface provided by the infrastructure does not assert control over the originating medical devices or additional data sources. The infrastructure does not inject commands, alter device behavior, or modify device configuration. Its role is limited to acquisition, normalization, attribution, and governed transport of data outputs. Any interpretation, analysis, or action based on the aggregated data streams is performed by downstream systems operating outside the scope of the infrastructure.

By enabling association of additional data sources at the infrastructure level, the disclosed system allows hospitals to introduce new measurement capabilities incrementally, without redesigning existing device installations or repeating device-level integration efforts. This approach supports heterogeneous device environments and long equipment lifecycles, while preserving a consistent data model and governance framework across both primary devices and auxiliary sources.

The extension interface capability described herein is an optional embodiment enabled by the retrofit integration infrastructure. It is not required to practice the core invention of retrofit medical device integration, but illustrates how the standardized, governed integration plane may serve as a foundation for future expansion of data acquisition and contextualization within a healthcare facility.

DETAILED DESCRIPTION OF THE FIGURES

FIG. 1—Medical Device Integration System with Wall-Mounted, Wall-Adjacent, or Wall-Associated Infrastructure and Device-Specific Interface Modules FIG. 1 illustrates a non-limiting example of a medical device integration (MDI) system comprising wall-mounted, wall-adjacent, or wall-associated infrastructure components and device-specific interface modules deployed at a point of care. FIG. 1 further illustrates an example of a core retrofit architecture and clinical integration spine, including bedside retrofit installation, enforcement of an isolated clinical integration plane, coexistence with incumbent vendor systems, and generation of standardized data objects.

A device-interface module, referred to herein as an Device-Interface Module (110), is shown as a component configured to acquire output data from a medical device and to normalize device-specific signals into a standardized internal representation suitable for governed transport within a clinical integration plane. The Device-Interface Module (110) may include one or more device communication interfaces (111) configured to exchange data with a connected medical device using a supported protocol. In some embodiments, the Device-Interface Module (110) further includes a combined power-and-data interface (112) configured to receive electrical power and data over a single physical connection. In some embodiments, the Device-Interface Module (110) includes a pass-through or parallel communication interface (113) configured to allow continued communication between a medical device and a third-party or incumbent vendor monitoring system while enabling acquisition of a parallel copy of device output data. In some embodiments, the Device-Interface Module (110) includes an auxiliary power or data interface (114) configured to provide supplemental connectivity or power. In some embodiments, the Device-Interface Module (110) includes a wireless communication module (115) configured to exchange data using one or more short-range or local wireless communication protocols.

The Device-Interface Module (110) is communicatively coupled via a wired data communication cable (125) to a power-and-data distribution component (120). In some embodiments, an additional patch cable (126) may be used to interconnect nearby components within the installation footprint. The power-and-data distribution component (120) is configured to provide controlled power delivery and network connectivity to one or more device-interface modules operating within the clinical integration plane.

The power-and-data distribution component (120) includes one or more front-facing distribution ports (121), each configured to connect to a respective device-interface module. The distribution component (120) further includes one or more rear-facing distribution ports (122) configured to provide power or data connectivity to upstream or downstream infrastructure components. In some embodiments, the distribution component (120) includes an expansion or interconnection port (123) configured to couple the distribution component to another distribution component or network element. The distribution component (120) may include an embedded portion (124) configured to be located within a wall cavity or enclosure and an exposed portion (127) accessible from the room environment.

The power-and-data distribution component (120) is communicatively coupled to an edge processing unit (130) via an interconnection cable (137). The edge processing unit (130) operates as a network authority for the clinical integration plane and is configured to manage discovery, authentication, authorization, buffering, logging, and routing of standardized data objects.

The edge processing unit (130) may include an infrastructure network interface (132) configured to connect to a facility network infrastructure (180). In some embodiments, the edge processing unit (130) includes a power-and-data interface (133) configured to receive electrical power and data. The edge processing unit (130) may include an embedded portion (134) configured to be located within a wall cavity or enclosure.

In some embodiments, the system includes a wireless access component (135) configured to support wireless communication with device-interface modules or auxiliary infrastructure components. In some embodiments, the system further includes an alternate wireless communication path (136) configured to provide continuity of connectivity when another communication path is unavailable or degraded.

The clinical integration plane illustrated in FIG. 1 is structurally segregated from the general hospital information technology network. All ingress and egress of device data is mediated by the edge processing unit (130), which enforces authorization, isolation, and routing policies before standardized data objects are transmitted to downstream systems via the facility network infrastructure (180).

FIG. 1 illustrates architectural relationships among components and data paths for explanatory purposes only and does not limit the number, arrangement, power sources, communication paths, physical packaging, or internal implementation of the disclosed system elements.

Figure 2:
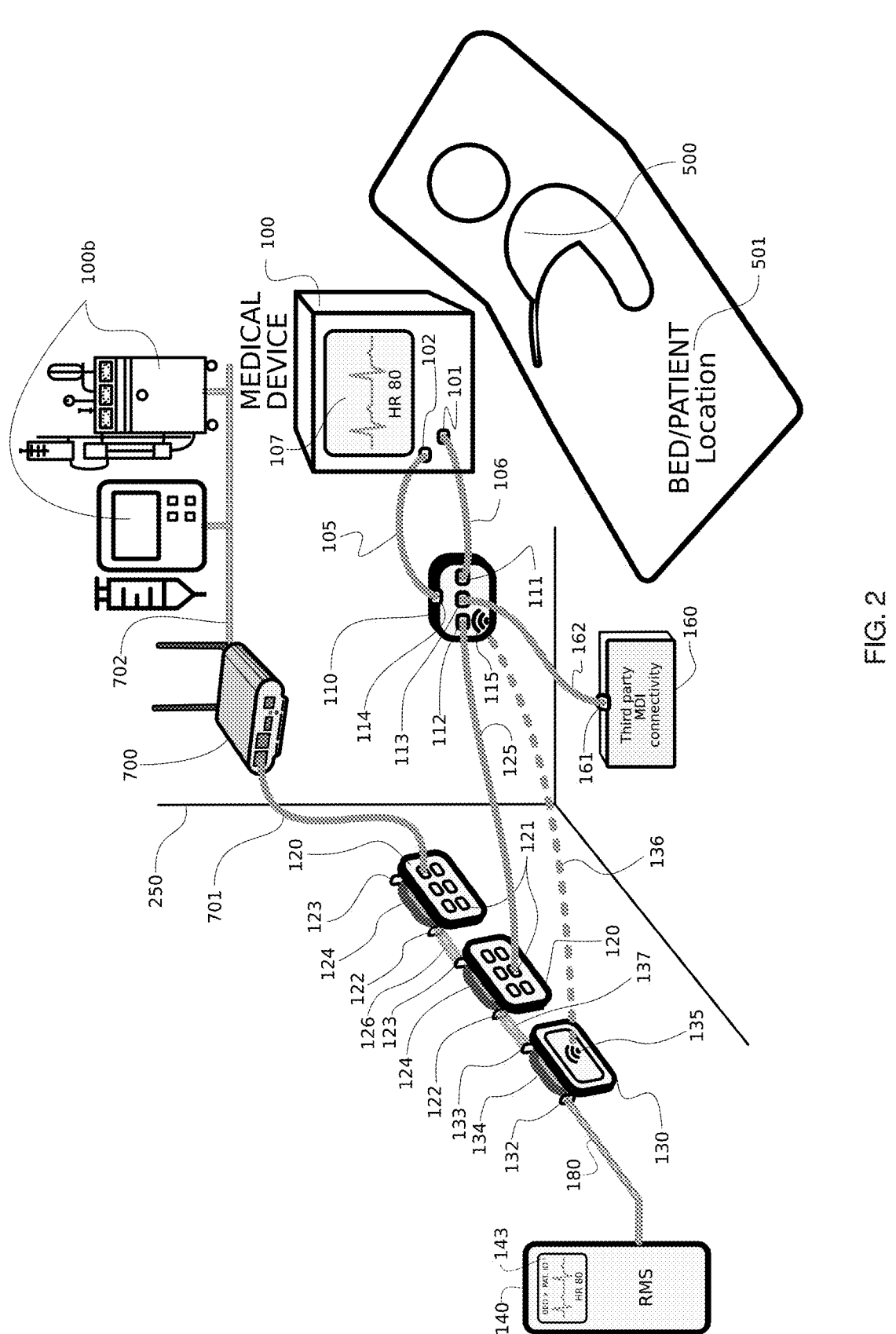
FIG. 2 is a system-level architectural diagram illustrating an integrated clinical IoT environment in which multiple medical devices, device-interface modules, wall-mounted power-and-data distribution components, edge processing units, legacy device interfaces, and remote systems cooperate to provide governed medical data integration.

FIG. 2—Integrated Clinical Device Integration Architecture with Wall-Mounted, Wall-Adjacent, or Wall-Associated Infrastructure FIG. 2 illustrates a non-limiting example of an integrated clinical device integration architecture in which medical devices are connected to a wall-mounted, wall-adjacent, or wall-associated infrastructure that provides governed data acquisition, edge processing, and secure routing to downstream systems within an existing healthcare facility.

At a point of care, one or more medical devices (100) are positioned in association with a patient (500) and a corresponding bed or care location (501). Each medical device (100) may generate physiologic or operational data and may present information locally via a medical device display (107). Device output data may be made available via a medical device data interface (101). In some embodiments, the medical device (100) may optionally provide accessory power via an optional power interface (102).

Each medical device (100) is coupled to a dedicated device-interface module, referred to herein as an Device-Interface Module (110), via a device-specific connection assembly (106). In some embodiments, the Device-Interface Module (110) may further receive power or data via a device-interface module power or data connector (105). The Device-Interface Module (110) is configured to acquire device output data and to normalize device-specific signals into a standardized internal representation suitable for governed transport within a clinical integration plane.

The Device-Interface Module (110) may include a device communication interface (111) configured to exchange data with the connected medical device. In some embodiments, the Device-Interface Module (110) includes a combined power and data interface (112) configured to receive electrical power and data over a single physical connection. In some embodiments, the Device-Interface Module (110) includes a pass-through or parallel communication interface (113) configured to allow continued communication between the medical device and a third-party or incumbent vendor monitoring system while enabling acquisition of a parallel copy of device output data. In some embodiments, the Device-Interface Module (110) includes an auxiliary power or data interface (114). In some embodiments, the Device-Interface Module (110) includes a wireless communication module (115) configured to exchange data using one or more wireless communication protocols.

One or more Device-Interface Modules (110) are communicatively coupled via a data communication cable (125) or a patch cable (126) to a power-and-data distribution component (120). The power-and-data distribution component (120) may be mounted on, within, or behind a wall or structural surface (250). The distribution component (120) includes one or more front-facing distribution ports (121) configured to connect to device-interface modules. In some embodiments, the distribution component (120) includes one or more rear-facing distribution ports (122). In some embodiments, the distribution component (120) includes an expansion or interconnection port (123). The distribution component (120) may further include an embedded portion (124) configured to be located within a wall cavity or enclosure.

The power-and-data distribution component (120) operates as part of a controlled clinical integration plane and is communicatively coupled to an edge processing unit (130) via an interconnection cable (137). The edge processing unit (130) functions as a network authority for the clinical integration plane and is configured to manage discovery, authentication, authorization, buffering, logging, and routing of standardized data objects.

The edge processing unit (130) may include an infrastructure network interface (132) configured to connect to a facility network infrastructure (180). In some embodiments, the edge processing unit (130) includes a power and data interface (133). In some embodiments, the edge processing unit (130) includes an embedded portion (134) configured to be located within a wall or enclosure.

In some embodiments, the architecture supports optional wireless communication paths. A wireless access component (135) may provide wireless connectivity between infrastructure components. In some embodiments, an alternate wireless communication path (136) may be used to maintain continuity of data transport when a primary communication path is unavailable or degraded.

In some embodiments, standardized data objects generated within the clinical integration plane are routed to a remote management system (140) via the facility network infrastructure (180). In some embodiments, standardized data objects may be streamed in real time or retrieved from buffered storage using a data streaming capability (143). The nature and functionality of downstream systems are implementation-dependent and are not limiting.

In some embodiments, legacy medical devices (100b) are integrated into the architecture using third-party connectivity hardware (160). Such hardware may include a third-party device interface (161) configured to couple to a legacy medical device. In some embodiments, a third-party connection cable (162) is used to connect the legacy medical device to the third-party connectivity hardware (160). The third-party connectivity hardware (160) may be coupled to the power-and-data distribution component (120) using a legacy medical device interface (700). In some embodiments, an interface connection cable (701) couples the legacy medical device interface (700) to the distribution component (120). In some embodiments, a legacy device connection cable (702) couples the legacy medical device to the legacy medical device interface (700).

The clinical integration plane illustrated in FIG. 2 is structurally segregated from the general hospital information technology network. Medical devices and device-interface modules do not obtain direct connectivity to the hospital IT network. All ingress and egress of device data is mediated by the edge processing unit (130), which enforces authorization, isolation, and routing policies before standardized data objects are transmitted to downstream systems.

FIG. 2 illustrates functional relationships among components and data paths for explanatory purposes only and does not limit the number, arrangement, connectivity, power sources, physical packaging, processing allocation, or internal implementation of the illustrated components.

Figure 3:
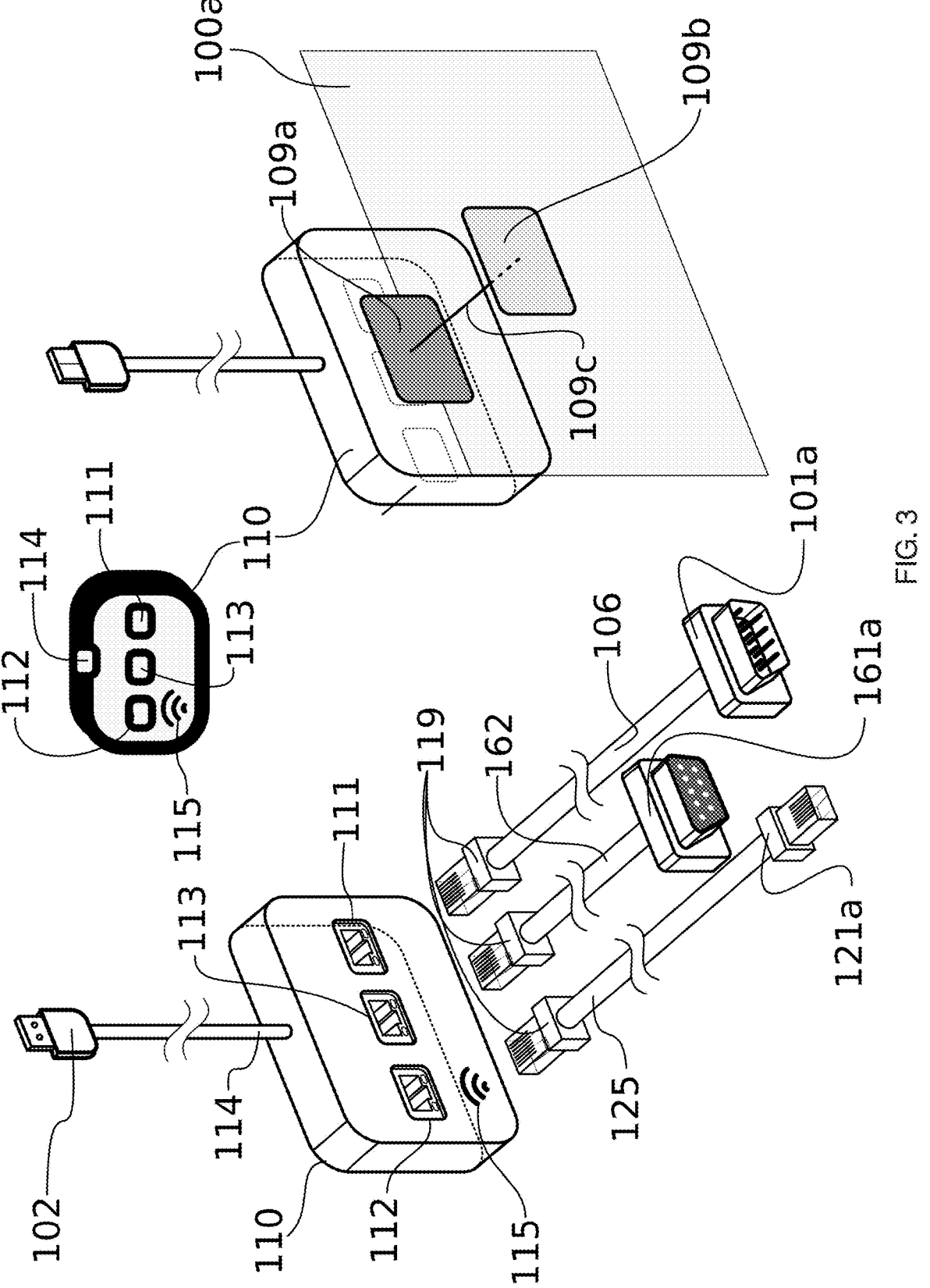
FIG. 3 is a perspective and exploded view illustrating an example device-interface module configured for attachment to a medical device, including representative ports, connectors, and attachment features.

FIG. 3—Device-Interface Module

FIG. 3 illustrates a non-limiting example of a device-interface module, referred to herein as an Device-Interface Module (110), configured to provide a physical and logical interface between a medical device and a clinical integration infrastructure.

The Device-Interface Module (110) is configured to be coupled to an external enclosure of a medical device (100a). In some embodiments, coupling is achieved using a device-specific connection assembly (106) selected to match the physical and electrical characteristics of the medical device. The device-interface module is configured to receive device output data from the medical device and to normalize device-specific signals into a standardized internal representation suitable for governed transport within a clinical integration plane.

In some embodiments, the Device-Interface Module (110) includes a device-interface module connector (101a) configured to mechanically and electrically mate with a corresponding medical device data interface. In some embodiments, the Device-Interface Module (110) may receive electrical power from the medical device via an optional power interface (102), when such power is made available by the medical device or an associated structure.

The Device-Interface Module (110) includes a device communication interface (111) configured to exchange data with the connected medical device. In some embodiments, the Device-Interface Module (110) includes a combined power and data interface (112) configured to receive electrical power and data over a single physical connection. In some embodiments, the Device-Interface Module (110) includes a pass-through or parallel communication interface (113) configured to allow continued communication between the medical device and a third-party system while enabling acquisition of a parallel copy of device output data. In some embodiments, the Device-Interface Module (110) includes an auxiliary power or data interface (114).

In some embodiments, the Device-Interface Module (110) includes a wireless communication module (115) configured to exchange data using one or more wireless communication protocols under selected operating conditions. The availability and use of wireless communication paths are optional and are not required in all embodiments.

The Device-Interface Module (110) may be communicatively coupled to downstream infrastructure using a data communication cable (125). In some embodiments, the Device-Interface Module (110) is configured to mate with a corresponding connector of a power-and-data distribution component using a mating connector (119). In some embodiments, the mating connection is configured to engage with a mating connector for a distribution port (121a).

In some embodiments, the Device-Interface Module (110) is configured to interface with third-party connectivity hardware using a matching interface on the device-interface module (161a). In such embodiments, a third-party connection cable (162) may be used to couple the Device-Interface Module (110) to the third-party connectivity hardware.

The Device-Interface Module (110) may further include one or more attachment elements configured to facilitate temporary physical attachment to the medical device enclosure. In some embodiments, the Device-Interface Module includes a device-interface module attachment element (109a). In some embodiments, the Device-Interface Module cooperates with a complementary attachment element (109b) affixed to the medical device enclosure. In some embodiments, coupling between the attachment elements is achieved along an attachment motion or alignment path (109c). The attachment mechanism may be removable and selected to accommodate clinical workflow, cleaning practices, and device servicing requirements.

In some embodiments, the Device-Interface Module (110) implements one or more security, buffering, integrity-checking, or status-reporting functions to support reliable data acquisition and transmission within the clinical integration infrastructure. The extent and allocation of such functions are implementation-dependent and are not limiting.

FIG. 3 is illustrative only and does not limit the size, shape, materials, internal circuitry, number of interfaces, signaling modes, power arrangements, attachment mechanisms, or functional partitioning of the device-interface module.

Figure 4:
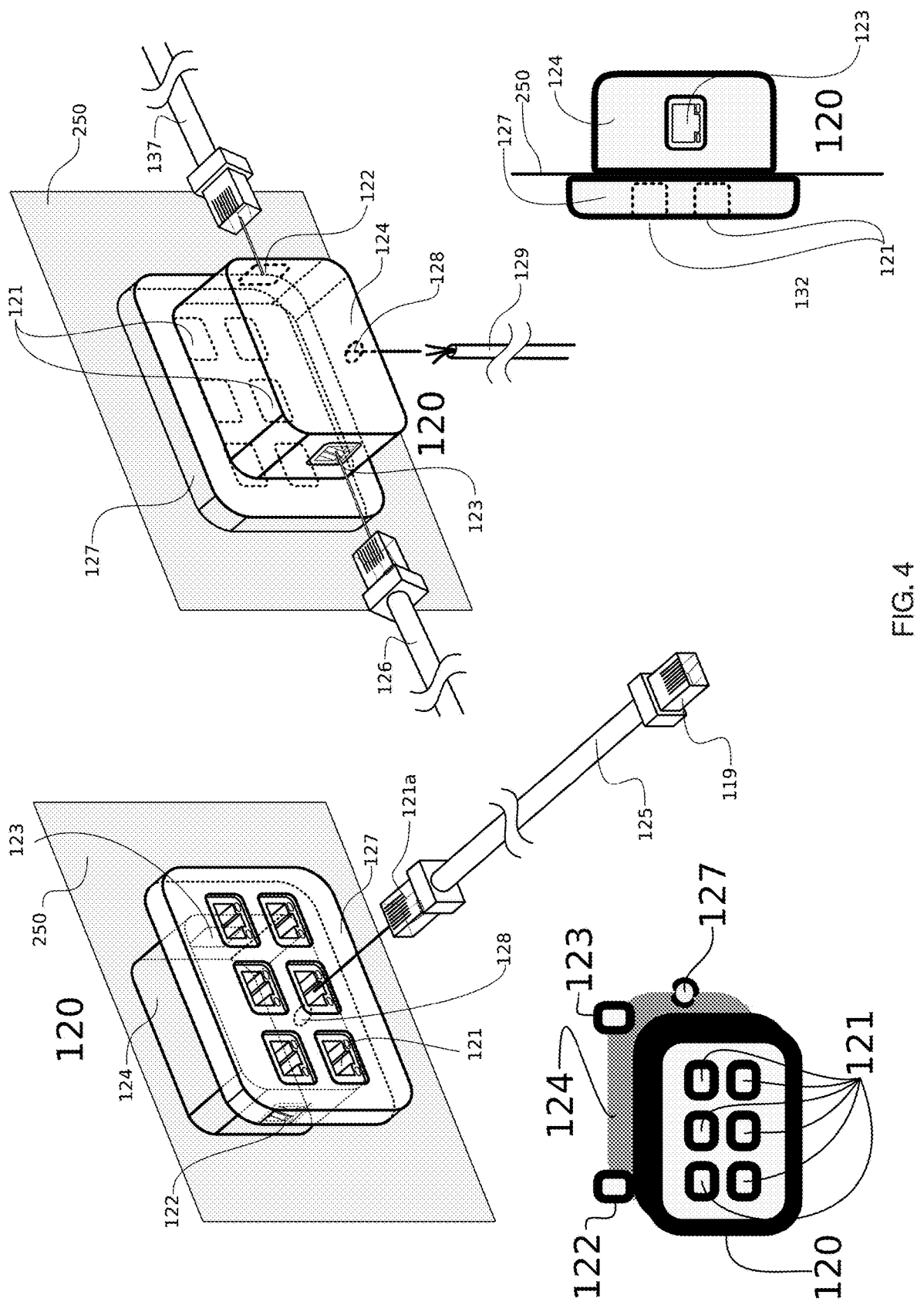
FIG. 4 is a perspective and sectional view illustrating an example wall-mounted or wall-embedded power-and-data distribution component showing externally accessible ports and concealed infrastructure connections.

FIG. 4—Wall-Mounted Power-and-Data Distribution Component

FIG. 4 illustrates a non-limiting example of a wall-mounted power-and-data distribution component (120) configured for use as part of a retrofit clinical integration infrastructure.

The power-and-data distribution component (120) is mounted at, within, or behind a wall or structural surface (250). In some embodiments, the distribution component (120) is installed within an existing wall cavity or enclosure without requiring structural modification. The distribution component (120) includes an externally accessible portion (127) that is exposed to the clinical environment and permits connection of downstream components.

The externally accessible portion (127) includes one or more front-facing distribution ports (121). Each front-facing distribution port (121) is configured to provide power and data connectivity to a downstream device-interface module or other authorized component within a controlled clinical integration plane. In some embodiments, a front-facing distribution port (121) is configured to mate with a corresponding connector using a mating connector (121*a*). In some embodiments, a mating connector (119) is used to mechanically and electrically engage a downstream cable or device with the front-facing distribution port (121).

The distribution component (120) further includes a wall-embedded portion (124) that houses infrastructure-side connections. In some embodiments, the wall-embedded portion (124) includes a rear-facing distribution port (122) configured to provide power and data connectivity to another infrastructure component. In some embodiments, the wall-embedded portion (124) includes an expansion or interconnection port (123) configured to interconnect the distribution component (120) with another distribution component or a network element within the clinical integration plane.

The distribution component (120) is configured to exchange data using one or more data communication cables (125). In some embodiments, a patch cable (126) is used to interconnect nearby infrastructure components. In some embodiments, an interconnection cable (137) is used to couple the distribution component (120) to an edge processing unit or another infrastructure element.

The distribution component (120) includes a power input interface (128) configured to receive electrical power from a facility power source. In some embodiments, a power supply cable (129) is coupled to the power input interface (128) to deliver electrical power to the distribution component (120). Electrical power received at the distribution component (120) may be selectively delivered to downstream devices over power-and-data connections.

In some embodiments, the distribution component (120) includes one or more infrastructure network interfaces (132) configured to support controlled communication with an edge processing unit or other authorized infrastructure components. The distribution component (120) operates under coordination with an edge processing unit and does not provide unrestricted access to a general hospital information technology network.

The separation between the externally accessible portion (127) and the wall-embedded portion (124) allows clinical-side access to downstream connections while maintaining organization, protection, and concealment of backbone cabling within the wall. This arrangement supports retrofit deployment using existing wall structures and minimizes exposed cabling within patient care environments.

FIG. 4 is illustrative only and does not limit the number, arrangement, port roles, power delivery techniques, physical dimensions, mounting mechanisms, internal circuitry, or interconnection topology of the power-and-data distribution component.

Figure 5:
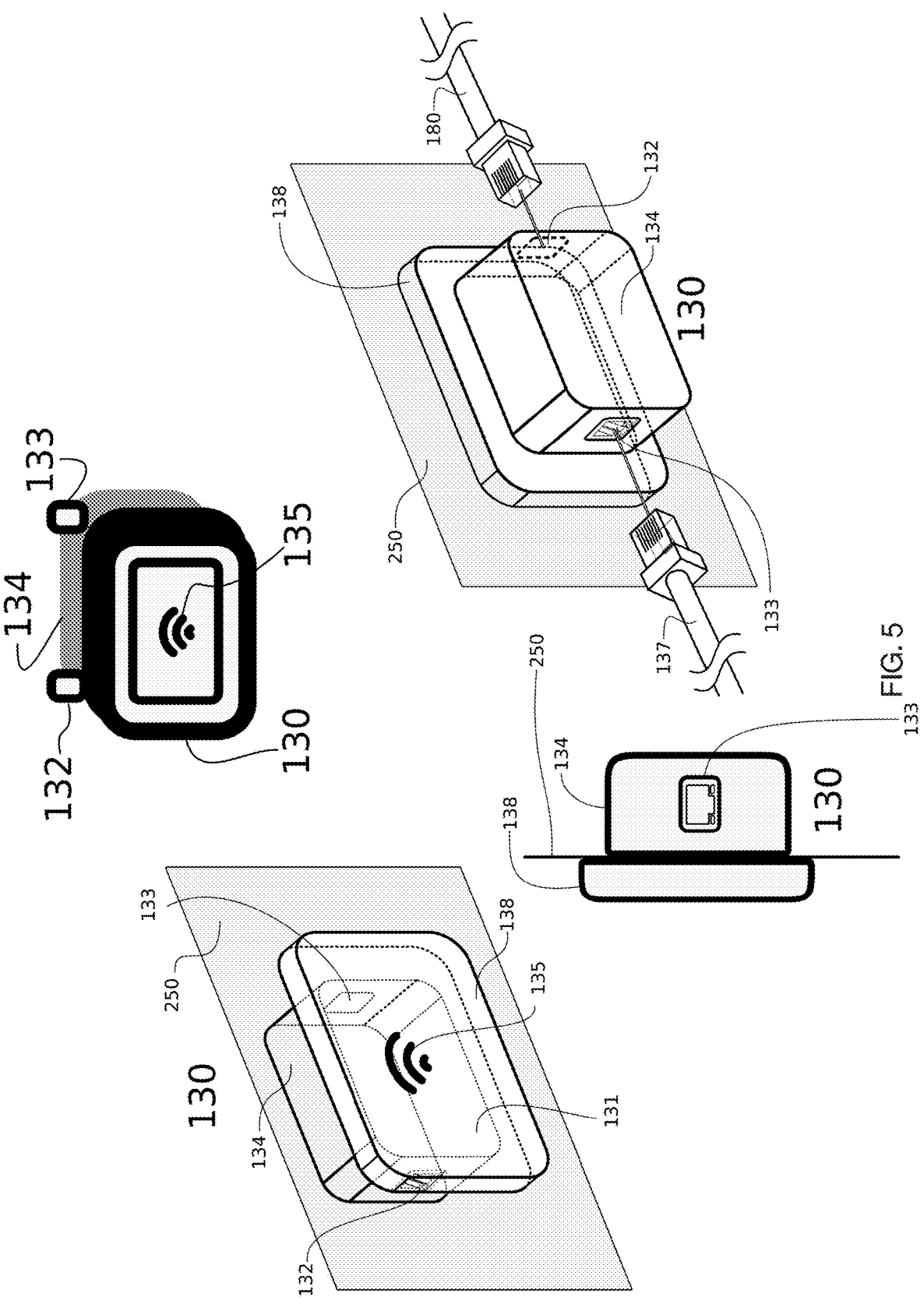
FIG. 5 is a perspective and sectional view illustrating an example wall-mounted or wall-embedded edge processing unit with representative external interfaces and concealed infrastructure connections.

FIG. 5—Wall-Mounted Edge Processing Unit

FIG. 5 illustrates a non-limiting example of a wall-mounted edge processing unit (130) configured for use as part of a retrofit clinical integration infrastructure.

The edge processing unit (130) is installed at, within, or behind a wall or structural surface (250). In some embodiments, the edge processing unit (130) includes a wall-embedded portion (134) positioned within an existing wall cavity or enclosure. The wall-embedded portion (134) houses processing, networking, and power-related components while remaining concealed from the clinical environment.

The edge processing unit (130) further includes a visible portion (131) that is accessible from the clinical environment. The visible portion (131) may include one or more externally perceptible indicators or interfaces providing status or operational visibility. In some embodiments, the visible portion (131) is designed to minimize exposed controls or connectors while preserving accessibility for inspection or maintenance.

The wall-embedded portion (134) includes one or more infrastructure network interfaces (132). Each infrastructure network interface (132) is configured to support wired communication with another infrastructure component operating within a controlled clinical integration plane. The wall-embedded portion (134) further includes one or more power-and-data interfaces (133). Each power-and-data interface (133) is configured to receive electrical power and data over a wired connection from an upstream distribution component or other authorized infrastructure element.

In some embodiments, the edge processing unit (130) is communicatively coupled to an infrastructure network (180). Communication with the infrastructure network (180) permits controlled exchange of standardized data objects with authorized downstream systems or management services while maintaining isolation of the clinical integration plane from a general hospital information technology network.

The edge processing unit (130) may be coupled to other infrastructure components using an interconnection cable (137). The interconnection cable (137) provides a controlled physical link between the edge processing unit (130) and one or more distribution components or upstream aggregation elements.

In some embodiments, the edge processing unit (130) includes a wireless access component (135). The wireless access component (135) is configured to support wireless communication with authorized device-interface modules or auxiliary infrastructure components under selected operating conditions. The presence and use of wireless communication are optional and are not required in all embodiments.

The edge processing unit (130) is configured to receive standardized data objects originating from device-interface modules through the controlled clinical integration plane. The edge processing unit (130) enforces authorization, isolation, buffering, time alignment, and routing of standardized data objects prior to delivery to authorized downstream destinations.

The wall-mounted configuration of the edge processing unit (130) enables retrofit deployment using existing wall structures while minimizing visible equipment in patient care areas. The separation between the visible portion (131) and the wall-embedded portion (134) supports clean installation, controlled access, and protection of infrastructure-side cabling.

FIG. 5 is illustrative only and does not limit the physical dimensions, mounting arrangement, number or type of interfaces, internal processing allocation, wireless capabilities, power delivery techniques, or operational roles of the edge processing unit.

Figure 6:
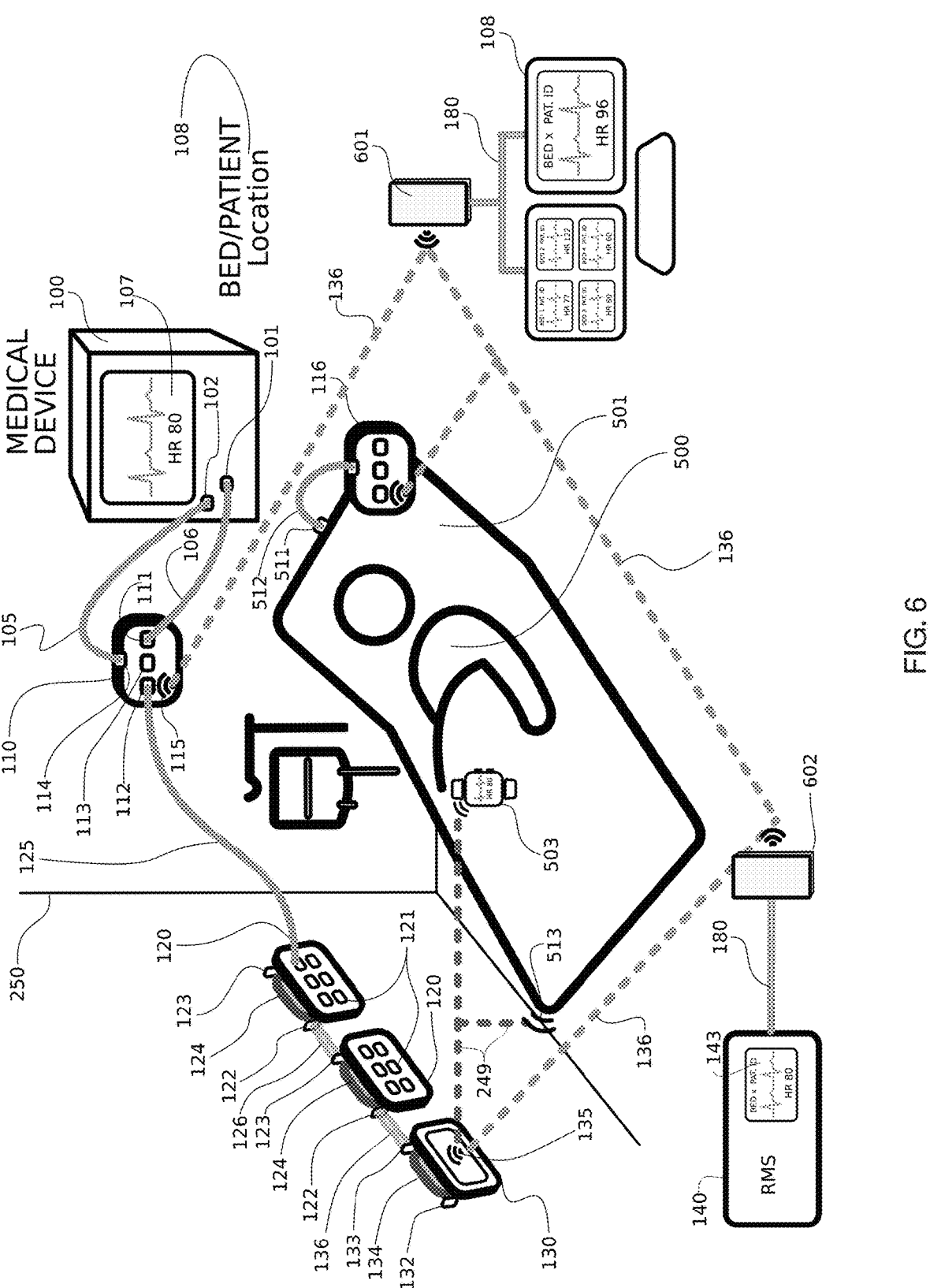
FIG. 6 is a conceptual diagram illustrating a patient-centric clinical integration topology in which multiple bedside medical devices, wearable or personal sensors, distribution components, edge processing units, and remote systems are communicatively coupled through wired and optional wireless communication paths.

FIG. 6—Patient-Centric Clinical Integration Topology

FIG. 6 illustrates a non-limiting example of a patient-centric clinical integration topology in which multiple medical devices and auxiliary sensing components associated with a patient are coupled to a retrofit clinical integration infrastructure.

As shown, a patient (500) is associated with a bed or physical care location (501). One or more medical devices (100) are positioned at or near the bed or care location (501). Each medical device (100) may generate physiologic or operational data and may present information locally via a display (107). The medical device (100) may provide output data through a medical device data interface (101). In some embodiments, the medical device (100) may optionally provide accessory power through an optional power interface (102).

A device-interface module (110) is coupled to the medical device (100) by a device-specific connection assembly (106). The device-interface module (110) is configured to receive device output data and to normalize device-specific signals into a standardized internal representation suitable for governed transport within a clinical integration plane. In some embodiments, the device-interface module (110) includes a device communication interface (111) configured to exchange data with the medical device (100). In some embodiments, the device-interface module (110) includes a combined power and data interface (112) configured to receive electrical power and data over a single physical connection. In some embodiments, the device-interface module (110) includes a pass-through or parallel communication interface (113) configured to allow continued communication between the medical device (100) and a third-party or incumbent vendor monitoring system (108). In some embodiments, the device-interface module (110) includes an auxiliary power or data interface (114). In some embodiments, the device-interface module (110) includes a wireless communication module (115).

In some embodiments, the device-interface module (110) receives power from a bed-integrated interface (511). In some embodiments, the device-interface module (110) is coupled to the bed-integrated interface (511) by a bed-to-module connection cable (512). In some embodiments, the bed or associated structure supports a bed wireless communication protocol (513) for exchange of bed-related or contextual information.

In addition to fixed medical devices, one or more personal monitoring devices (503) associated with the patient (500) may generate additional patient-related or contextual data. In some embodiments, the personal monitoring device (503) communicates using a personal wireless network (249). Data from the personal monitoring device (503) may be received by a device-interface module (110) or by an edge processing unit (130) and incorporated into the clinical integration plane.

In some embodiments, an auxiliary device-interface module (116) is associated with a physical asset such as the bed or care-area structure. The auxiliary device-interface module (116) is configured to communicate wirelessly with the clinical integration infrastructure and to acquire contextual or environmental data associated with the bed, care location, or patient environment.

One or more device-interface modules (110) are communicatively coupled by a data communication cable (125) to a power and data distribution component (120). In some embodiments, a patch cable (126) is used for interconnection between nearby components. The power and data distribution component (120) includes one or more front-facing distribution ports (121) configured to connect to device-interface modules. The power and data distribution component (120) further includes one or more rear-facing distribution ports (122). In some embodiments, the power and data distribution component (120) includes an expansion or interconnection port (123). In some embodiments, the power and data distribution component (120) includes an embedded portion (124) positioned within a wall or enclosure (250).

The power and data distribution component (120) operates under control of an edge processing unit (130). The edge processing unit (130) includes an infrastructure network interface (132) configured to communicate with an infrastructure network (180). The edge processing unit (130) further includes a power and data interface (133). In some embodiments, the edge processing unit (130) includes an embedded portion (134) positioned within a wall or enclosure (250).

In some embodiments, the edge processing unit (130) includes a wireless access component (135). In some embodiments, the system supports an alternate wireless communication path (136). In some embodiments, communication between infrastructure components is supported by one or more interconnection cables (137).

In some embodiments, standardized data objects generated within the clinical integration plane are routed through the infrastructure network (180) to a remote management system (140). In some embodiments, the remote management system (140) supports a data streaming capability (143) for real-time access or retrieval of stored data.

In some embodiments, a wireless-to-wired bridge (601) provides connectivity between wireless components and wired infrastructure. In some embodiments, an independent wireless access point (602) provides wireless communication capability independent of a facility information technology network.

FIG. 6 illustrates relationships among medical devices, device-interface modules, auxiliary sensing components, and infrastructure elements in a patient-centric topology. The figure is provided for explanatory purposes only and does not limit the number, arrangement, communication paths, power sources, processing locations, or deployment configurations of the disclosed system.

FIG. 7—Retrofit Deployment Using Existing Wall Plate Locations and Alternative Mounting Structures FIG. 7 illustrates a non-limiting example of retrofit deployment of the disclosed medical device integration infrastructure using existing facility mounting locations within a healthcare environment. FIG. 7 is presented as a set of related views, including FIGS. 7A-7G, which together illustrate representative conditions before, during, and after installation, as well as alternative mounting configurations. The illustrated arrangements are exemplary and are provided for explanatory clarity only, and do not define a required order, method, or installation procedure.

FIG. 7A illustrates an existing wall location including one or more conventional wall plates mounted to a wall surface and associated with an internal wall cavity or enclosure. Such wall plates may include, by way of example, blank cover plates, electrical outlet plates, switch plates, or low-voltage termination plates commonly present in patient rooms or care areas. These wall plate locations represent pre-existing facility infrastructure available for retrofit installation.

FIG. 7B illustrates a representative retrofit condition in which at least one existing wall plate has been removed, displaced, overlaid, or otherwise made available for installation of a clinical integration node. In this condition, the existing wall cavity and enclosure may be reused as an installation anchor, without requiring structural modification of the wall, installation of new conduit, or alteration of the surrounding room layout.

FIG. 7C illustrates a representative post-installation condition in which a clinical integration node occupies substantially the same wall footprint as the prior wall plate and may utilize the same internal wall cavity. In some embodiments, the clinical integration node replaces a blank plate; in other embodiments, it replaces or is positioned adjacent to an electrical outlet or other wall-mounted fixture. Multiple wall plate positions along a wall may be selectively converted to clinical integration nodes, while other wall plates remain unchanged, thereby supporting incremental and flexible retrofit deployment.

FIG. 7D illustrates an embodiment in which the clinical integration node is housed within a surface-mounted enclosure affixed to a wall surface and positioned over or adjacent to an existing wall opening. In this configuration, the enclosure provides a wall-adjacent mounting arrangement that does not require full in-wall installation and accommodates facilities where wall depth, obstructions, or policies limit in-wall mounting.

FIG. 7E illustrates a hybrid mounting embodiment in which the clinical integration node is partially received within an existing wall cavity while extending outward in a surface-mounted enclosure. This configuration enables reuse of existing wall cavities while providing flexibility in enclosure depth, interface accessibility, and installation constraints.

FIG. 7F illustrates a fully surface-mounted embodiment in which the clinical integration node is mounted externally to a wall without occupying a wall cavity. Such embodiments may be employed where wall penetration is restricted, where rapid or temporary deployment is desired, or where existing wall infrastructure cannot be modified.

FIG. 7G illustrates a non-wall-mounted embodiment in which the clinical integration node is mounted to a pole, IV pole, column, rail, or other structural support within a care environment. In this configuration, the clinical integration node provides equivalent functional behavior to wall-mounted embodiments while enabling deployment in mobile, temporary, or reconfigurable care settings, including bedside poles and transport environments.

Across all embodiments illustrated in FIG. 7, the clinical integration node may include one or more powered network interfaces, internal control circuitry, and processing components, as described elsewhere herein. However, the internal composition, number of interfaces, physical dimensions, external appearance, enclosure geometry, mounting mechanism, and functional allocation of the node are implementation-dependent and not limited by the illustrated representations.

FIG. 7 does not depict internal electronics, wiring, fastening hardware, tools, or installer actions, and is not intended to constrain the disclosed infrastructure to any particular installation technique, enclosure form factor, or mounting orientation. Collectively, FIG. 7 demonstrates that the disclosed infrastructure supports retrofit deployment using existing facility infrastructure as well as alternative mounting structures, without requiring structural renovation and without limiting the invention to in-wall installations.

LIST OF REFERENCE NUMERALS

100—Medical Device

A clinical device configured to generate patient-related or device-related data and having at least one physical interface through which such data may be made available to an external component.

100*a*—Medical Device External Enclosure

An outer housing of the medical device (100), which may include one or more surfaces suitable for temporary or removable attachment of an accessory component.

100*b*—Legacy Medical Device

A medical device configured to communicate using an interface or protocol that differs from those used by other devices in the system, and which may be coupled to the integration infrastructure through an intermediary interface.

101—Medical Device Data Interface

A physical connector or port provided on a medical device and configured to make device output data available to an external component.

101*a*—Device-Interface Module Connector

A connector provided on a device-interface module and configured to mechanically and electrically mate with the medical device data interface (101).

102—Optional Power Interface

A power interface provided by a medical device or associated structure and configured to supply electrical power to an attached accessory.

105—Device-Interface Module Power or Data Connector

A connector and associated cable configured to supply power and, in some embodiments, data to a device-interface module.

106—Device-Specific Connection Assembly

A cable or connector assembly configured to couple a device-interface module to a corresponding medical device using a device-appropriate interface.

107—Medical Device Display

A visual output element of the medical device (100) configured to present information to clinical personnel.

108—Third-Party or Incumbent Vendor Monitoring System

An external system configured to receive data from one or more medical devices using an incumbent communication pathway.

109*a*—Device-Interface Module Attachment Element

A removable attachment element coupled to a device-interface module and configured to facilitate temporary physical attachment.

109*b*—Complementary Attachment Element

A complementary attachment element affixed to a medical device enclosure and configured to engage with the attachment element (109*a*).

109*c*—Attachment Motion or Alignment Path

A relative motion or alignment used when coupling the device-interface module to the medical device enclosure.

110—Device-Interface Module

A module configured to couple to a medical device and acquire device output data for entry into the integration infrastructure. The module may include one or more interfaces for data acquisition, power reception, and communication with other infrastructure components.

111—Device Communication Interface

A communication interface provided on the device-interface module and configured to exchange data with a medical device using a supported protocol.

112—Combined Power and Data Interface

An interface configured to receive both electrical power and data over a single physical connection.

113—Pass-Through or Parallel Communication Interface

An interface configured to allow continued communication between a medical device and a third-party system while also enabling acquisition of a copy of device output data.

114—Auxiliary Power or Data Interface

An interface configured to provide electrical power to, or exchange data with, the device-interface module.

115—Wireless Communication Module

A wireless communication component configured to exchange data using one or more short-range or local wireless protocols.

116—Wireless Device-Interface Module Associated with a Physical Asset

A device-interface module configured to communicate wirelessly with the integration infrastructure and to be associated with a bed, stretcher, chair, or other physical structure, and to acquire contextual or environmental data.

119—Mating Connector

A connector configured to mechanically and electrically mate with one or more corresponding interfaces.

120—Power and Data Distribution Component

A distribution component configured to provide power and data connectivity to one or more device-interface modules and to operate under control of an edge processing component.

121—Front-Facing Distribution Port

A port provided on the power and data distribution component and configured to connect to a device-interface module.

121*a*—Mating Connector for Distribution Port

A connector configured to mate with the distribution port (121).

122—Rear-Facing Distribution Port

A port configured to provide power and/or data connectivity to another infrastructure component.

123—Expansion or Interconnection Port

A port configured to interconnect the distribution component with another distribution component or network element.

124—Embedded Portion of Distribution Component

A portion of the distribution component configured to be located within a wall cavity or enclosure.

125—Data Communication Cable

A wired communication cable configured to transmit data and, in some embodiments, electrical power.

126—Patch Cable

A short communication cable configured to interconnect nearby components.

127—Exposed Portion of Distribution Component

A portion of the distribution component accessible from the room environment.

128—Power Input Interface

An interface configured to receive electrical power from a facility power source.

129—Power Supply Cable

A cable configured to supply electrical power to the distribution component.

130—Edge Processing Unit

A processing component configured to manage discovery, authorization, data normalization, buffering, and routing within a clinical integration plane.

131—Edge Processing Unit Front Panel

An externally visible portion of the edge processing unit.

132—Infrastructure Network Cable

A network wired cable connect the edge processing unit (131) to a facility network.

133—Power and Data Interface for Edge Processing Unit

An interface configured to supply power and data to the edge processing unit.

134—Embedded Portion of Edge Processing Unit

A portion of the edge processing unit configured to be located within a wall or enclosure.

135—Wireless Access Component

A wireless component configured to support communication with one or more wireless device-interface modules.

136—Alternate Wireless Communication Path

A wireless communication path configured to provide connectivity when another path is unavailable.

137—Interconnection Cable

A cable configured to interconnect the distribution component and the edge processing unit.

138—Exposed Portion of Edge Processing Unit

A visible portion of the edge processing unit accessible from the room environment.

140—Remote Management System

A system configured to monitor, manage, or update one or more infrastructure components.

143—Data Streaming Capability

A capability to provide access to data in real time or from stored records.

160—Third-Party Connectivity Hardware

Hardware configured to interface between a medical device and the integration infrastructure.

161—Third-Party Device Interface

An interface provided on third-party connectivity hardware and configured to couple to a medical device.

161*a*—Matching Interface on Device-Interface Module

An interface on the device-interface module configured to mate with the third-party device interface (161).

162—Third-Party Connection Cable

A cable configured to connect a medical device to third-party connectivity hardware.

180—Facility Network Infrastructure

A wired network infrastructure provided by a facility.

249—Personal Wireless Network

A wireless network configured for short-range communication with personal or wearable devices.

250—Wall or Structural Surface

A wall or structural element of a facility used as a mounting or embedding surface.

500—Patient

An individual receiving care within the facility.

501—Bed or Care Location

A physical location associated with a patient.

503—Personal Monitoring Device

A device configured to acquire patient-related data and communicate wirelessly.

511—Bed-Integrated Interface

An interface integrated into a bed or similar structure and configured to provide power or data.

512—Bed-to-Module Connection Cable

A cable configured to connect a device-interface module to a bed-integrated interface.

513—Bed Wireless Communication Protocol

A wireless protocol configured to transmit data associated with bed state or condition.

601—Wireless-to-Wired Bridge

A device configured to bridge wireless communication to a wired network.

602—Independent Wireless Access Point

A wireless access component configured to operate independently of a facility IT network.

700—Legacy Medical Device Interface

An interface component configured to couple legacy medical devices to the integration infrastructure.

701—Interface Connection Cable

A cable configured to connect the legacy medical device interface to the distribution component.

702—Legacy Device Connection Cable

A cable configured to connect a legacy medical device to the legacy medical device interface.

The invention claimed is:

1. A retrofit medical device integration infrastructure for deployment in an already-built healthcare facility without structural renovation, comprising:

(a) a plurality of device-interface modules, each device-interface module being configured to be physically coupled to a respective medical device at a point of care and comprising (i) a device-specific connector configured to receive output data from the respective medical device; and (ii) protocol translation circuitry configured to normalize device-specific output signals into a standardized internal representation;

(b) a power-and-data distribution component installed at an existing bedside wall location corresponding to an electrical outlet position or low-voltage wall box, the power-and-data distribution component comprising a plurality of powered connection ports configured to provide controlled power and data connectivity to the plurality of device-interface modules, and the powered connection ports forming fixed physical attachment points within a clinical integration plane; and (c) an edge processing unit mounted on, within, or adjacent to the wall and coupled to the power-and-data distribution component, the edge processing unit comprising one or more processors and memory and being configured to establish and enforce a controlled clinical integration plane that is structurally and logically isolated from a general hospital information technology network, wherein the edge processing unit is configured to:

(i) automatically detect a physical connection event corresponding to a device-interface module being connected to a powered connection port, (ii) authenticate and authorize the device-interface module in response to the connection event before accepting output data, (iii) assign a physical location to the device-interface module based at least in part on an identity of the powered connection port, and (iv) generate standardized data objects from the normalized output data, the standardized data objects including device identity information, location information, and time information;

wherein the edge processing unit is further configured to route the standardized data objects to at least one downstream system through a secure communication path while preventing the medical devices and device-interface modules from obtaining direct connectivity to the general hospital information technology network; and wherein the infrastructure is configured to operate in coexistence with an incumbent vendor monitoring pathway by acquiring a parallel copy of the medical device output data for entry into the clinical integration plane, while allowing the respective medical device to continue communicating over an existing primary communication pathway with an incumbent vendor monitoring or central station system.

2. The system of claim 1, wherein the power-and-data distribution component is dimensioned to fit within or behind a wall footprint corresponding to a standard electrical outlet box or standard low-voltage enclosure.

3. The system of claim 1, wherein the powered connection ports comprise power-over-ethernet ports, and wherein the edge processing unit is configured to selectively disable power delivery on an individual powered connection port in response to a failure of authentication or authorization of a connected device-interface module.

4. The system of claim 1, wherein each device-interface module comprises a pass-through interface configured to maintain the primary communication pathway between the respective medical device and an incumbent vendor monitoring system, while providing the parallel copy of the output data to the clinical integration plane.

5. The system of claim 1, wherein the edge processing unit is configured to maintain time synchronization for the standardized data objects using at least one of network time protocol, precision time protocol, or a hardware time synchronization signal.

6. The system of claim 1, wherein the edge processing unit is configured to buffer standardized data objects in local storage during an interruption of upstream connectivity and to forward buffered standardized data objects in time order based on the time information.

7. The system of claim 1, wherein the secure communication path comprises at least one alternate uplink selected from a wireless uplink or a secondary wired uplink, that is used when a primary uplink is unavailable.

8. The system of claim 1, wherein the edge processing unit is configured to apply a room template comprising a mapping between powered connection ports and location identifiers, and to assign the physical location based on the mapping.

9. The system of claim 1, wherein the edge processing unit is configured to detect movement of a medical device by detecting a disconnection of a device-interface module from a first powered connection port and a subsequent connection of the device-interface module to a second powered connection port, and to update the assigned physical location and log the movement with time information.

10. The system of claim 1, further comprising an electrical-backhaul path including a receptacle module coupled to existing facility electrical wiring and a receiver/bridge module, wherein the receiver/bridge module is configured to transport the standardized data objects to an aggregation point or uplink without requiring installation of new network cabling at the point of care.

11. A method of retrofitting an existing healthcare facility to provide governed medical device integration without structural renovation, comprising:

installing, at or near a bedside electrical outlet location, a wall-mounted or in-wall power-and-data distribution component comprising a plurality of powered connection ports;

installing a wall-mounted or in-wall edge processing unit coupled to the power-and-data distribution component and configured to enforce a clinical integration plane isolated from a general hospital information technology network;

for each of a plurality of medical devices in a care area, physically coupling a dedicated device-interface module to the medical device, the device-interface module being configured to receive device output data and to normalize the device output data into a standardized internal representation;

connecting each device-interface module to a respective powered connection port; at the edge processing unit, detecting a connection event corresponding to a device-interface module being connected to a powered connection port, authenticating and authorizing the device-interface module, and assigning a physical location based at least in part on an identity of the powered connection port;

generating standardized data objects from the normalized output data, the standardized data objects including device identity information, location information, and time information;

routing the standardized data objects to at least one downstream system through a secure communication path, while preventing the medical devices from obtaining direct connectivity to the general hospital information technology network; and maintaining coexistence with an incumbent vendor monitoring pathway by coupling the device-interface module to obtain a parallel copy of the device output data, while allowing the medical device to continue communicating with an incumbent vendor monitoring system over a primary communication pathway.

12. The method of claim 11, wherein installing the power-and-data distribution component and the edge processing unit comprises wiring within a wall cavity or within a standard electrical wall box or low-voltage enclosure at the bedside electrical outlet location.

13. The method of claim 11, wherein physically coupling a dedicated device-interface module comprises selecting a device-interface module validated for a specific medical device model and coupling the selected device-interface module to the medical device without requiring device-level protocol configuration by hospital information technology personnel.

14. The method of claim 11, further comprising applying a predefined room template to assign location identifiers to the powered connection ports, and assigning the physical location based on the room template.

* * * * *